(12) United States Patent
Fulkerson et al.

(10) Patent No.: US 9,198,687 B2
(45) Date of Patent: Dec. 1, 2015

(54) ACUTE STROKE REVASCULARIZATION/RECANALIZATION SYSTEMS PROCESSES AND PRODUCTS THEREBY

(75) Inventors: John Fulkerson, Rancho Santo Margarita, CA (US); David A. Ferrera, Redondo Beach, CA (US); Andrew Cragg, Edina, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/123,390

(22) Filed: May 19, 2008

(65) Prior Publication Data

US 2009/0105737 A1    Apr. 23, 2009

Related U.S. Application Data

(60) Provisional application No. 60/980,736, filed on Oct. 17, 2007, provisional application No. 61/044,392, filed on Apr. 11, 2008, provisional application No. 61/015,154, filed on Dec. 19, 2007, provisional (Continued)

(51) Int. Cl.
*A61F 2/06* (2013.01)
*A61B 17/3207* (2006.01)
(Continued)

(52) U.S. Cl.
CPC ........... *A61B 17/3207* (2013.01); *A61B 17/221* (2013.01); *A61B 17/320725* (2013.01);
(Continued)

(58) Field of Classification Search
CPC ............. A61B 17/221; A61B 17/3207; A61B 17/32056; A61B 2/01; A61B 2/013; A61B 17/320725; A61B 2017/00867; A61B 2017/22094; A61F 2/91
USPC ............ 604/93.01, 96.01, 507; 606/191–192, 606/194, 200; 623/1.1–1.12, 1.15–1.16, 623/1.34, 1.39–1.4
See application file for complete search history.

(56) References Cited

U.S. PATENT DOCUMENTS 2,709,999 A  6/1955 Nagel
3,174,851 A  3/1965 Buehler et al.
(Continued)

FOREIGN PATENT DOCUMENTS

EP  0321912  6/1989
EP  820729 A1  1/1998
(Continued)

OTHER PUBLICATIONS

Micro Therapeutics, Inc., DBA EV3 Neurovascular, Inc., Solitaire FR Revascularization Device, Instructions for Use, 70494-001 Rev, Mar. 2009.
(Continued)

*Primary Examiner* — Ashley Fishback
(74) *Attorney, Agent, or Firm* — Mark J. Kertz, Esq.

(57) ABSTRACT

An acute stroke recanalization system and processes include catheter-based improved reconstrainable or tethered neurological devices which are deliverable through highly constricted and tortuous vessels, crossing the zone associated with subject thrombi/emboli, where deployment impacts, addresses or bridges the embolus, compacting the same into luminal walls which enables perfusion and lysis of the embolus, while the improved neurological medical device itself remains contiguous with the delivery system acting as a filter, basket or stand alone stenting mechanism, depending on the status of the embolus and other therapeutic aspects of the treatment being offered for consideration.

22 Claims, 38 Drawing Sheets

Related U.S. Application Data application No. 60/989,422, filed on Nov. 20, 2007, provisional application No. 60/987,384, filed on Nov. 12, 2007, provisional application No. 61/019,506, filed on Jan. 7, 2008.

(51) Int. Cl.

| | | |
|---|---|---|
| *A61B 17/221* | (2006.01) | |
| *A61F 2/82* | (2013.01) | |
| *A61M 29/02* | (2006.01) | |
| A61B 17/00 | (2006.01) | |
| A61B 17/22 | (2006.01) | |
| A61F 2/01 | (2006.01) | |
| A61M 25/10 | (2013.01) | |

(52) U.S. Cl.
CPC .................. *A61F2/82* (2013.01); *A61M 29/02* (2013.01); *A61B 2017/00845* (2013.01); *A61B 2017/00867* (2013.01); *A61B 2017/22038* (2013.01); *A61B 2017/22082* (2013.01); *A61F 2/013* (2013.01); *A61F 2250/0059* (2013.01); *A61M 2025/1095* (2013.01); *A61M 2025/1097* (2013.01)

(56) References Cited

U.S. PATENT DOCUMENTS

| | | | |
|---|---|---|---|
| 3,351,463 A | 11/1967 | Rozner et al. | |
| 3,506,171 A | 4/1970 | Rupert | |
| 3,753,700 A | 8/1973 | Harrison et al. | |
| 4,650,466 A | 3/1987 | Luther | |
| 4,993,481 A | 2/1991 | Kamimoto et al. | |
| 4,998,539 A | 3/1991 | Delsanti | |
| 5,035,686 A | 7/1991 | Crittenden et al. | |
| 5,057,114 A * | 10/1991 | Wittich et al. | 606/127 |
| 5,222,964 A | 6/1993 | Cooper | |
| 5,222,971 A | 6/1993 | Willard et al. | |
| 5,275,622 A | 1/1994 | Lazarus et al. | |
| 5,312,344 A | 5/1994 | Grinfeld et al. | |
| 5,327,885 A | 7/1994 | Griffith | |
| 5,344,395 A | 9/1994 | Whalen | |
| 5,370,653 A * | 12/1994 | Cragg | 606/170 |
| 5,425,739 A | 6/1995 | Jessen | |
| 5,449,372 A | 9/1995 | Schmaltz | |
| 5,456,667 A | 10/1995 | Ham et al. | |
| 5,527,282 A | 6/1996 | Segal | |
| 5,643,309 A | 7/1997 | Myler et al. | |
| 5,649,906 A | 7/1997 | Gory et al. | |
| 5,653,743 A | 8/1997 | Martin | |
| 5,681,336 A | 10/1997 | Clement et al. | |
| 5,683,449 A | 11/1997 | Marcade | |
| 5,695,469 A | 12/1997 | Segal | |
| 5,718,724 A | 2/1998 | Goicoechea et al. | |
| 5,792,157 A | 8/1998 | Mische | |
| 5,795,322 A | 8/1998 | Boudewijn | |
| 5,800,457 A | 9/1998 | Gelbfish | |
| 5,800,519 A | 9/1998 | Sandock | |
| 5,827,324 A | 10/1998 | Cassell et al. | |
| 5,853,419 A | 12/1998 | Imran | |
| 5,916,235 A | 6/1999 | Gugliemlim | |
| 5,922,019 A | 7/1999 | Hankh et al. | |
| 5,928,260 A | 7/1999 | Chin | |
| 5,938,671 A | 8/1999 | Katoh | |
| 5,938,697 A | 8/1999 | Killion et al. | |
| 5,941,895 A | 8/1999 | Myler et al. | |
| 5,947,995 A | 9/1999 | Samuels | |
| 5,951,599 A | 9/1999 | McCrory | |
| 5,961,547 A | 10/1999 | Razavi | |
| 5,968,013 A | 10/1999 | Smith et al. | |
| 5,972,016 A | 10/1999 | Morales | |
| 5,972,157 A | 10/1999 | Engelson | |
| 5,972,219 A | 10/1999 | Habets | |
| 5,976,120 A | 11/1999 | Chow et al. | |
| 5,980,514 A | 11/1999 | Kupiecki et al. | |
| 6,001,118 A | 12/1999 | Daniel et al. | |
| 6,010,449 A | 1/2000 | Selmon et al. | |
| 6,010,498 A | 1/2000 | Guglielmi | |
| 6,010,521 A | 1/2000 | Lee et al. | |
| 6,015,424 A | 1/2000 | Rosenbluth et al. | |
| 6,039,721 A | 3/2000 | Johnson et al. | |
| 6,051,020 A | 4/2000 | Goicoechea et al. | |
| 6,063,070 A | 5/2000 | Eder | |
| 6,063,104 A | 5/2000 | Villar et al. | |
| 6,063,111 A | 5/2000 | Hieshima et al. | |
| 6,066,149 A | 5/2000 | Samson et al. | |
| 6,066,158 A | 5/2000 | Engelson | |
| 6,093,199 A | 7/2000 | Brown et al. | |
| 6,096,034 A | 8/2000 | Kupiecki et al. | |
| 6,106,548 A | 8/2000 | Roubin et al. | |
| 6,117,167 A | 9/2000 | Goicoechea et al. | |
| 6,123,115 A | 9/2000 | Greenhalgh | |
| 6,136,006 A | 10/2000 | Johnson et al. | |
| 6,146,396 A | 11/2000 | Konya et al. | |
| 6,159,238 A | 12/2000 | Killion et al. | |
| 6,159,239 A | 12/2000 | Greenhalgh | |
| 6,164,339 A | 12/2000 | Greenhalgh | |
| 6,168,592 B1 | 1/2001 | Kupiecki et al. | |
| 6,168,604 B1 | 1/2001 | Cano | |
| 6,190,358 B1 | 2/2001 | Fitzmaurice | |
| 6,192,944 B1 | 2/2001 | Greenhalgh | |
| 6,193,708 B1 | 2/2001 | Ken et al. | |
| 6,210,364 B1 | 4/2001 | Anderson | |
| 6,217,609 B1 | 4/2001 | Haverkost | |
| 6,221,096 B1 | 4/2001 | Aiba et al. | |
| 6,231,598 B1 | 5/2001 | Berry et al. | |
| 6,238,430 B1 * | 5/2001 | Klumb et al. | 623/1.11 |
| 6,280,413 B1 | 8/2001 | Clark et al. | |
| 6,283,940 B1 | 9/2001 | Mulholland | |
| 6,283,992 B1 | 9/2001 | Hankh et al. | |
| 6,290,720 B1 | 9/2001 | Khosravi et al. | |
| 6,302,906 B1 | 10/2001 | Goicoechea et al. | |
| 6,305,436 B1 | 10/2001 | Andersen et al. | |
| 6,306,141 B1 | 10/2001 | Jervis | |
| 6,312,459 B1 * | 11/2001 | Huang et al. | 623/1.15 |
| 6,322,585 B1 | 11/2001 | Khosravi et al. | |
| 6,325,815 B1 | 12/2001 | Kusleika et al. | |
| 6,325,820 B1 | 12/2001 | Khosravi et al. | |
| 6,325,822 B1 | 12/2001 | Chouinard et al. | |
| 6,344,041 B1 | 2/2002 | Kupiecki et al. | |
| 6,383,205 B1 | 5/2002 | Samson et al. | |
| 6,390,993 B1 | 5/2002 | Cornish et al. | |
| 6,402,771 B1 | 6/2002 | Palmer et al. | |
| 6,454,780 B1 | 9/2002 | Wallace | |
| 6,458,139 B1 | 10/2002 | Palmer et al. | |
| 6,468,301 B1 * | 10/2002 | Amplatz et al. | 623/1.13 |
| 6,475,236 B1 | 11/2002 | Roubin et al. | |
| 6,475,237 B2 | 11/2002 | Drasler | |
| 6,485,500 B1 | 11/2002 | Kokish | |
| 6,485,509 B2 | 11/2002 | Killion et al. | |
| 6,537,294 B1 | 3/2003 | Boyle et al. | |
| 6,551,341 B2 | 4/2003 | Boylan et al. | |
| 6,551,342 B1 | 4/2003 | Shen et al. | |
| 6,553,810 B2 | 4/2003 | Webb et al. | |
| 6,554,842 B2 | 4/2003 | Heuser et al. | |
| 6,554,856 B1 | 4/2003 | Doorly et al. | |
| 6,558,405 B1 | 5/2003 | McInnes | |
| 6,562,066 B1 | 5/2003 | Martin | |
| 6,569,179 B2 | 5/2003 | Teoh et al. | |
| 6,569,193 B1 | 5/2003 | Cox et al. | |
| 6,575,997 B1 | 6/2003 | Palmer et al. | |
| 6,589,265 B1 | 7/2003 | Palmer et al. | |
| 6,592,607 B1 | 7/2003 | Palmer et al. | |
| 6,592,615 B1 | 7/2003 | Marcade et al. | |
| 6,605,057 B2 | 8/2003 | Fitzmaurice | |
| 6,610,077 B1 | 8/2003 | Hancock et al. | |
| 6,616,617 B1 | 9/2003 | Ferrera et al. | |
| 6,629,953 B1 | 10/2003 | Boyd | |
| 6,632,241 B1 | 10/2003 | Hancock et al. | |
| 6,635,081 B2 | 10/2003 | Khosravi et al. | |
| 6,638,294 B1 | 10/2003 | Palmer | |
| 6,641,590 B1 | 11/2003 | Palmer et al. | |
| 6,652,505 B1 | 11/2003 | Tsugita | |
| 6,652,576 B1 | 11/2003 | Stalker | |

(56) References Cited

U.S. PATENT DOCUMENTS

| | | | |
|---|---|---|---|
| 6,660,021 B1 | 12/2003 | Palmer et al. | |
| 6,663,607 B2 | 12/2003 | Slaikeu et al. | |
| 6,666,829 B2 | 12/2003 | Cornish et al. | |
| 6,669,723 B2 | 12/2003 | Killion et al. | |
| 6,673,025 B1 | 1/2004 | Richardson et al. | |
| 6,685,722 B1 | 2/2004 | Rosenbluth | |
| 6,685,738 B2 | 2/2004 | Chouinard et al. | |
| 6,695,813 B1 | 2/2004 | Boyle et al. | |
| 6,702,843 B1 | 3/2004 | Brown et al. | |
| 6,709,440 B2 | 3/2004 | Callol et al. | |
| 6,716,178 B1 | 4/2004 | Kilpatrick et al. | |
| 6,723,112 B2 | 4/2004 | Ho et al. | |
| 6,730,104 B1 | 5/2004 | Sepetka et al. | |
| 6,733,519 B2 | 5/2004 | Lashinski | |
| 6,746,468 B1 | 6/2004 | Sepetka et al. | |
| 6,764,506 B2 | 7/2004 | Roubin et al. | |
| 6,773,454 B2 | 8/2004 | Wholey et al. | |
| 6,790,237 B2 | 9/2004 | Stinson | |
| 6,795,979 B2 | 9/2004 | Fournier | |
| 6,802,851 B2 | 10/2004 | Jones et al. | |
| 6,818,015 B2 | 11/2004 | Hankh et al. | |
| 6,821,291 B2 | 11/2004 | Bolea et al. | |
| 6,824,558 B2 | 11/2004 | Parodi | |
| 6,833,003 B2 | 12/2004 | Jones et al. | |
| 6,840,958 B2 | 1/2005 | Nunez et al. | |
| 6,881,220 B2 | 4/2005 | Edwin et al. | |
| 6,893,413 B2 | 5/2005 | Martin | |
| 6,913,612 B2 | 7/2005 | Palmer et al. | |
| 6,949,620 B2 | 9/2005 | Aida et al. | |
| 6,953,472 B2 | 10/2005 | Palmer et al. | |
| 6,955,685 B2 | 10/2005 | Escamilla et al. | |
| 6,960,227 B2 | 11/2005 | Jones et al. | |
| 6,991,641 B2 | 1/2006 | Diaz | |
| 6,994,723 B1 | 2/2006 | McMahon | |
| 7,001,422 B2 | 2/2006 | Escamilla et al. | |
| 7,004,954 B1 | 2/2006 | Voss | |
| 7,004,955 B2 | 2/2006 | Shen et al. | |
| 7,004,956 B2 | 2/2006 | Palmer et al. | |
| 7,018,401 B1 | 3/2006 | Hyodoh et al. | |
| 7,029,688 B2 | 4/2006 | Hubbell et al. | |
| 7,037,329 B2 | 5/2006 | Martin | |
| 7,041,116 B2 | 5/2006 | Goto et al. | |
| 7,048,014 B2 | 5/2006 | Hyodoh et al. | |
| 7,056,328 B2 | 6/2006 | Arnott | |
| 7,056,336 B2 | 6/2006 | Armstrong et al. | |
| 7,060,091 B2 | 6/2006 | Killion et al. | |
| 7,089,218 B1 | 8/2006 | Visel | |
| 7,112,217 B1 | 9/2006 | Kugler et al. | |
| 7,118,600 B2 | 10/2006 | Dua et al. | |
| 7,125,419 B2 | 10/2006 | Sequin et al. | |
| 7,128,736 B1 | 10/2006 | Abrams et al. | |
| 7,144,421 B2 | 12/2006 | Carpenter et al. | |
| 7,147,655 B2 | 12/2006 | Chermoni | |
| 7,147,660 B2 | 12/2006 | Chobotov et al. | |
| 7,156,869 B1 | 1/2007 | Pacetti | |
| 7,160,317 B2 | 1/2007 | McHale | |
| 7,169,165 B2 | 1/2007 | Belef et al. | |
| 7,172,575 B2 | 2/2007 | El-Nounou | |
| 7,172,617 B2 | 2/2007 | Colgan | |
| 7,175,607 B2 | 2/2007 | Lim | |
| 7,179,273 B1 * | 2/2007 | Palmer et al. | 606/200 |
| 7,179,284 B2 | 2/2007 | Khosravi et al. | |
| 7,201,769 B2 | 4/2007 | Jones et al. | |
| 7,201,770 B2 | 4/2007 | Johnson | |
| 7,223,284 B2 | 5/2007 | Khosravi et al. | |
| 7,238,197 B2 | 7/2007 | Sequin et al. | |
| 7,240,516 B2 | 7/2007 | Pryor | |
| 7,241,301 B2 | 7/2007 | Thramann et al. | |
| 7,279,003 B2 | 10/2007 | Berra et al. | |
| 7,279,292 B2 | 10/2007 | Imam et al. | |
| 7,285,126 B2 | 10/2007 | Sepetka et al. | |
| 7,294,147 B2 | 11/2007 | Hartley | |
| 7,300,458 B2 | 11/2007 | Henkes et al. | |
| 7,306,619 B1 | 12/2007 | Palmer | |
| 7,309,345 B2 | 12/2007 | Wallace | |
| 7,309,351 B2 | 12/2007 | Escamilla | |
| 7,323,000 B2 | 1/2008 | Monstdt et al. | |
| 7,323,005 B2 | 1/2008 | Wallace et al. | |
| 7,323,006 B2 | 1/2008 | Andreas et al. | |
| 7,326,240 B1 | 2/2008 | Caro et al. | |
| 7,344,550 B2 | 3/2008 | Carrison et al. | |
| 7,344,556 B2 | 3/2008 | Seguin et al. | |
| 7,351,255 B2 | 4/2008 | Andreas | |
| 7,354,455 B2 | 4/2008 | Stinson | |
| 7,402,169 B2 | 7/2008 | Killion et al. | |
| 7,407,509 B2 | 8/2008 | Greenberg et al. | |
| 7,435,254 B2 | 10/2008 | Chouinard et al. | |
| 7,438,720 B2 | 10/2008 | Shaked | |
| 7,455,646 B2 | 11/2008 | Richardson et al. | |
| 7,473,272 B2 | 1/2009 | Pryor | |
| 7,494,474 B2 | 2/2009 | Richardson et al. | |
| 7,549,974 B2 | 6/2009 | Nayak | |
| 7,691,122 B2 | 4/2010 | Dieck et al. | |
| 7,708,704 B2 * | 5/2010 | Mitelberg et al. | 600/585 |
| 7,727,242 B2 | 6/2010 | Sepetka et al. | |
| 7,727,243 B2 | 6/2010 | Sepetka et al. | |
| 7,749,243 B2 | 7/2010 | Phung | |
| 7,780,694 B2 | 8/2010 | Palmer et al. | |
| 7,833,240 B2 | 11/2010 | Okushi | |
| 7,972,342 B2 | 7/2011 | Gandhi et al. | |
| 8,052,640 B2 | 11/2011 | Fiorella et al. | |
| 8,062,307 B2 | 11/2011 | Sepetka et al. | |
| 8,066,757 B2 | 11/2011 | Ferrera et al. | |
| 8,070,791 B2 | 12/2011 | Ferrera et al. | |
| 8,088,140 B2 | 1/2012 | Ferrera et al. | |
| 8,100,918 B2 | 1/2012 | Gandhi et al. | |
| 8,100,935 B2 | 1/2012 | Rosenbluth et al. | |
| 8,105,333 B2 | 1/2012 | Sepetka et al. | |
| 8,197,493 B2 | 6/2012 | Ferrera | |
| 2001/0000797 A1 | 5/2001 | Mazzocchi | |
| 2001/0004705 A1 | 6/2001 | Killion et al. | |
| 2001/0010013 A1 | 7/2001 | Cox et al. | |
| 2001/0031981 A1 | 10/2001 | Evans | |
| 2001/0034531 A1 | 10/2001 | Ho et al. | |
| 2001/0044633 A1 | 11/2001 | Klint | |
| 2001/0044647 A1 | 11/2001 | Pinchuk et al. | |
| 2001/0047202 A1 | 11/2001 | Slaikeu et al. | |
| 2001/0051823 A1 | 12/2001 | Khosravi et al. | |
| 2002/0004681 A1 | 1/2002 | Teoh et al. | |
| 2002/0007210 A1 | 1/2002 | Chouinard et al. | |
| 2002/0016564 A1 | 2/2002 | Courtney et al. | |
| 2002/0016624 A1 | 2/2002 | Patterson | |
| 2002/0032479 A1 | 3/2002 | Hankh et al. | |
| 2002/0038142 A1 | 3/2002 | Khosravi et al. | |
| 2002/0038146 A1 | 3/2002 | Harry | |
| 2002/0052643 A1 | 5/2002 | Wholey et al. | |
| 2002/0068968 A1 | 6/2002 | Hupp | |
| 2002/0072790 A1 | 6/2002 | McGuckin, Jr. et al. | |
| 2002/0087209 A1 | 7/2002 | Edwin et al. | |
| 2002/0091355 A1 | 7/2002 | Hayden | |
| 2002/0095141 A1 | 7/2002 | Belef | |
| 2002/0143387 A1 | 10/2002 | Soetikno et al. | |
| 2002/0161377 A1 | 10/2002 | Rabkin | |
| 2002/0169458 A1 | 11/2002 | Connors, III | |
| 2002/0183831 A1 | 12/2002 | Rolando et al. | |
| 2002/0198588 A1 | 12/2002 | Armstrong et al. | |
| 2003/0004536 A1 | 1/2003 | Boylan et al. | |
| 2003/0023230 A1 | 1/2003 | Lewis et al. | |
| 2003/0023299 A1 | 1/2003 | Amplatz et al. | |
| 2003/0032941 A1 | 2/2003 | Boyle | |
| 2003/0032977 A1 | 2/2003 | Brady | |
| 2003/0040771 A1 | 2/2003 | Hyodoh et al. | |
| 2003/0040772 A1 | 2/2003 | Hyodoh et al. | |
| 2003/0055440 A1 | 3/2003 | Jones et al. | |
| 2003/0055451 A1 | 3/2003 | Jones et al. | |
| 2003/0074056 A1 | 4/2003 | Killion et al. | |
| 2003/0078605 A1 | 4/2003 | Bashiri | |
| 2003/0097114 A1 | 5/2003 | Ouriel et al. | |
| 2003/0105484 A1 | 6/2003 | Boyle | |
| 2003/0125791 A1 | 7/2003 | Sequin et al. | |
| 2003/0125798 A1 | 7/2003 | Martin | |
| 2003/0130719 A1 | 7/2003 | Martin | |
| 2003/0139796 A1 | 7/2003 | Sequin et al. | |
| 2003/0139803 A1 | 7/2003 | Sequin et al. | |

(56) References Cited

U.S. PATENT DOCUMENTS

| | | |
|---|---|---|
| 2003/0149475 A1 | 8/2003 | Hyodoh et al. |
| 2003/0153944 A1 | 8/2003 | Phung |
| 2003/0176914 A1 | 9/2003 | Rabkin et al. |
| 2003/0195554 A1* | 10/2003 | Shen et al. ............ 606/200 |
| 2003/0199921 A1 | 10/2003 | Palmer et al. |
| 2003/0204202 A1 | 10/2003 | Palmer et al. |
| 2004/0002752 A1 | 1/2004 | Griffin et al. |
| 2004/0006306 A1 | 1/2004 | Evans et al. |
| 2004/0006381 A1 | 1/2004 | Sequin et al. |
| 2004/0019322 A1 | 1/2004 | Hoffmann |
| 2004/0030378 A1 | 2/2004 | Khosravi et al. |
| 2004/0034386 A1 | 2/2004 | Fulton et al. |
| 2004/0049258 A1 | 3/2004 | Khosravi et al. |
| 2004/0054367 A1 | 3/2004 | Jimenez, Jr. et al. |
| 2004/0059259 A1 | 3/2004 | Cornish et al. |
| 2004/0059407 A1 | 3/2004 | Escamilla et al. |
| 2004/0068288 A1 | 4/2004 | Palmer et al. |
| 2004/0073300 A1 | 4/2004 | Chouinard et al. |
| 2004/0078071 A1 | 4/2004 | Escamilla et al. |
| 2004/0079429 A1 | 4/2004 | Miller et al. |
| 2004/0088002 A1 | 5/2004 | Boyle |
| 2004/0102838 A1 | 5/2004 | Killion et al. |
| 2004/0106979 A1 | 6/2004 | Goicoechea et al. |
| 2004/0114912 A1 | 6/2004 | Okamoto et al. |
| 2004/0117003 A1 | 6/2004 | Ouriel et al. |
| 2004/0147939 A1 | 7/2004 | Rabkin et al. |
| 2004/0153117 A1 | 8/2004 | Clubb et al. |
| 2004/0158307 A1 | 8/2004 | Jones et al. |
| 2004/0158312 A1 | 8/2004 | Chouinard et al. |
| 2004/0186562 A1 | 9/2004 | Cox |
| 2004/0193246 A1 | 9/2004 | Ferrera |
| 2004/0199201 A1 | 10/2004 | Kellett et al. |
| 2004/0215312 A1 | 10/2004 | Andreas |
| 2004/0215319 A1 | 10/2004 | Berra et al. |
| 2004/0249439 A1 | 12/2004 | Richter et al. |
| 2004/0254628 A1 | 12/2004 | Nazzaro et al. |
| 2004/0260385 A1 | 12/2004 | Jones et al. |
| 2005/0033334 A1 | 2/2005 | Santra et al. |
| 2005/0033349 A1 | 2/2005 | Jones et al. |
| 2005/0033409 A1 | 2/2005 | Burke et al. |
| 2005/0038447 A1* | 2/2005 | Huffmaster ............ 606/127 |
| 2005/0038468 A1 | 2/2005 | Panetta et al. |
| 2005/0038496 A1 | 2/2005 | Jones et al. |
| 2005/0049676 A1 | 3/2005 | Nazzaro et al. |
| 2005/0055047 A1 | 3/2005 | Greenhalgh |
| 2005/0060017 A1 | 3/2005 | Fischell |
| 2005/0075715 A1 | 4/2005 | Borges et al. |
| 2005/0080480 A1 | 4/2005 | Bolea et al. |
| 2005/0090857 A1 | 4/2005 | Kusleika et al. |
| 2005/0090888 A1 | 4/2005 | Hines et al. |
| 2005/0096726 A1 | 5/2005 | Sequin et al. |
| 2005/0102018 A1 | 5/2005 | Carpenter et al. |
| 2005/0107823 A1 | 5/2005 | Leone et al. |
| 2005/0119684 A1 | 6/2005 | Guterman |
| 2005/0125023 A1 | 6/2005 | Bates |
| 2005/0126979 A1 | 6/2005 | Lowe |
| 2005/0131515 A1 | 6/2005 | Cully et al. |
| 2005/0131516 A1 | 6/2005 | Greenhalgh |
| 2005/0159774 A1 | 7/2005 | Belef |
| 2005/0177228 A1 | 8/2005 | Solem et al. |
| 2005/0187612 A1 | 8/2005 | Edwin |
| 2005/0192661 A1 | 9/2005 | Griffen et al. |
| 2005/0209673 A1 | 9/2005 | Shaked |
| 2005/0209675 A1 | 9/2005 | Ton et al. |
| 2005/0209678 A1 | 9/2005 | Henkes et al. |
| 2005/0216050 A1 | 9/2005 | Sepetka et al. |
| 2005/0222583 A1 | 10/2005 | Cano |
| 2005/0222607 A1 | 10/2005 | Palmer et al. |
| 2005/0267570 A1 | 12/2005 | Shadduck |
| 2005/0277978 A1 | 12/2005 | Greenhalgh |
| 2006/0020285 A1 | 1/2006 | Niermann |
| 2006/0020321 A1 | 1/2006 | Parker |
| 2006/0025845 A1 | 2/2006 | Escamilla et al. |
| 2006/0025850 A1 | 2/2006 | Feller et al. |
| 2006/0030865 A1 | 2/2006 | Balg |
| 2006/0036281 A1 | 2/2006 | Patterson |
| 2006/0052816 A1 | 3/2006 | Bates et al. |
| 2006/0058833 A1 | 3/2006 | VanCamp |
| 2006/0058836 A1 | 3/2006 | Bose et al. |
| 2006/0058838 A1* | 3/2006 | Bose et al. ............ 606/200 |
| 2006/0074480 A1 | 4/2006 | Bales |
| 2006/0089703 A1 | 4/2006 | Escamilla et al. |
| 2006/0100663 A1 | 5/2006 | Palmer et al. |
| 2006/0106421 A1 | 5/2006 | Teoh |
| 2006/0106448 A1 | 5/2006 | Shaked |
| 2006/0122685 A1 | 6/2006 | Bonsignore et al. |
| 2006/0135947 A1 | 6/2006 | Soltesz et al. |
| 2006/0142841 A1 | 6/2006 | Khosravi et al. |
| 2006/0142849 A1 | 6/2006 | Killion et al. |
| 2006/0195172 A1 | 8/2006 | Luo et al. |
| 2006/0200048 A1 | 9/2006 | Furst |
| 2006/0200221 A1 | 9/2006 | Malewicz |
| 2006/0224180 A1* | 10/2006 | Anderson et al. ............ 606/200 |
| 2006/0229645 A1 | 10/2006 | Bonnette |
| 2006/0259119 A1 | 11/2006 | Rucker |
| 2006/0265054 A1 | 11/2006 | Greenhalgh et al. |
| 2006/0271090 A1 | 11/2006 | Shaked et al. |
| 2006/0276883 A1 | 12/2006 | Greenberg et al. |
| 2006/0287701 A1* | 12/2006 | Pal ............ 623/1.11 |
| 2006/0287704 A1 | 12/2006 | Hartley et al. |
| 2007/0032852 A1 | 2/2007 | Machek et al. |
| 2007/0043424 A1 | 2/2007 | Pryor |
| 2007/0043425 A1 | 2/2007 | Hartley et al. |
| 2007/0055299 A1 | 3/2007 | Ishimaru |
| 2007/0055358 A1 | 3/2007 | Krolik et al. |
| 2007/0055360 A1 | 3/2007 | Hanson et al. |
| 2007/0055365 A1 | 3/2007 | Greenberg et al. |
| 2007/0067011 A1 | 3/2007 | Krolik et al. |
| 2007/0073376 A1 | 3/2007 | Krolik et al. |
| 2007/0088387 A1 | 4/2007 | Eskridge et al. |
| 2007/0100425 A1 | 5/2007 | Sequin et al. |
| 2007/0118205 A1 | 5/2007 | Davidson et al. |
| 2007/0123972 A1 | 5/2007 | Greenberg et al. |
| 2007/0135826 A1 | 6/2007 | Zaver et al. |
| 2007/0135888 A1 | 6/2007 | Khosravi et al. |
| 2007/0141036 A1 | 6/2007 | Barrueta et al. |
| 2007/0142896 A1 | 6/2007 | Anderson et al. |
| 2007/0156170 A1 | 7/2007 | Hancock et al. |
| 2007/0156228 A1 | 7/2007 | Majercak et al. |
| 2007/0162109 A1 | 7/2007 | Davila et al. |
| 2007/0191866 A1 | 8/2007 | Palmer et al. |
| 2007/0191884 A1 | 8/2007 | Eskridge et al. |
| 2007/0191924 A1 | 8/2007 | Rudakov |
| 2007/0198028 A1 | 8/2007 | Miloslavski |
| 2007/0198030 A1 | 8/2007 | Martin |
| 2007/0198075 A1 | 8/2007 | Levy |
| 2007/0203452 A1 | 8/2007 | Mehta |
| 2007/0203559 A1 | 8/2007 | Freudenthal et al. |
| 2007/0208367 A1 | 9/2007 | Fiorella |
| 2007/0208371 A1 | 9/2007 | French et al. |
| 2007/0219621 A1 | 9/2007 | Hartley et al. |
| 2007/0225794 A1 | 9/2007 | Thramann et al. |
| 2007/0233236 A1 | 10/2007 | Pryor |
| 2007/0250040 A1 | 10/2007 | Provost et al. |
| 2007/0266542 A1 | 11/2007 | Melsheimer |
| 2007/0270932 A1 | 11/2007 | Headley et al. |
| 2007/0288034 A1 | 12/2007 | MacCollum et al. |
| 2007/0288037 A1 | 12/2007 | Cheng |
| 2007/0288080 A1 | 12/2007 | Maccollum et al. |
| 2007/0288083 A1 | 12/2007 | Hines |
| 2007/0299503 A1 | 12/2007 | Berra et al. |
| 2008/0001333 A1 | 1/2008 | Kleine et al. |
| 2008/0015558 A1 | 1/2008 | Harlan |
| 2008/0015682 A1 | 1/2008 | Majercak et al. |
| 2008/0033528 A1 | 2/2008 | Satasiya et al. |
| 2008/0039926 A1 | 2/2008 | Majercak et al. |
| 2008/0039930 A1 | 2/2008 | Jones et al. |
| 2008/0045995 A1 | 2/2008 | Guterman et al. |
| 2008/0046064 A1 | 2/2008 | Sequin et al. |
| 2008/0046072 A1 | 2/2008 | Laborde et al. |
| 2008/0051803 A1 | 2/2008 | Monjtadt |
| 2008/0058724 A1 | 3/2008 | Wallace |
| 2008/0071178 A1 | 3/2008 | Greenland et al. |
| 2008/0077175 A1 | 3/2008 | Palmer |

(56) References Cited

U.S. PATENT DOCUMENTS

| | | |
|---|---|---|
| 2008/0082159 A1 | 4/2008 | Tseng et al. |
| 2008/0086196 A1 | 4/2008 | Truckai et al. |
| 2008/0097495 A1 | 4/2008 | Feller et al. |
| 2008/0103477 A1 | 5/2008 | Jones |
| 2008/0103585 A1 | 5/2008 | Monjtadt |
| 2008/0109063 A1 | 5/2008 | Hancock et al. |
| 2008/0109067 A1 | 5/2008 | Caro et al. |
| 2008/0114445 A1 | 5/2008 | Melsheimer et al. |
| 2008/0125855 A1 | 5/2008 | Henkes et al. |
| 2008/0140107 A1 | 6/2008 | Bei |
| 2008/0140181 A1 | 6/2008 | Reynolds |
| 2008/0147100 A1 | 6/2008 | Wallace et al. |
| 2008/0161903 A1 | 7/2008 | Sequin et al. |
| 2008/0161936 A1 | 7/2008 | Feller et al. |
| 2008/0167708 A1 | 7/2008 | Molland et al. |
| 2008/0195140 A1 | 8/2008 | Myla |
| 2008/0200946 A1 | 8/2008 | Braun et al. |
| 2008/0208319 A1 | 8/2008 | Rabkin et al. |
| 2008/0221554 A1 | 9/2008 | O'Connor et al. |
| 2008/0221600 A1 | 9/2008 | Dieck et al. |
| 2008/0221664 A1 | 9/2008 | Bales et al. |
| 2008/0221671 A1 | 9/2008 | Chouinard et al. |
| 2008/0228216 A1 | 9/2008 | Strauss et al. |
| 2008/0234795 A1 | 9/2008 | Snow et al. |
| 2008/0243229 A1 | 10/2008 | Wallace et al. |
| 2008/0243232 A1 | 10/2008 | Hegg et al. |
| 2008/0247943 A1 | 10/2008 | Lanza |
| 2008/0249598 A1 | 10/2008 | Sherry |
| 2008/0255678 A1 | 10/2008 | Cully et al. |
| 2008/0262506 A1 | 10/2008 | Griffin |
| 2008/0262528 A1 | 10/2008 | Martin |
| 2008/0262532 A1 | 10/2008 | Martin |
| 2008/0262592 A1 | 10/2008 | Jordan |
| 2008/0262952 A1 | 10/2008 | Channell |
| 2008/0269774 A1* | 10/2008 | Garcia et al. .......... 606/127 |
| 2008/0269868 A1 | 10/2008 | Bei |
| 2008/0275497 A1 | 11/2008 | Palmer et al. |
| 2008/0275498 A1 | 11/2008 | Palmer et al. |
| 2008/0275536 A1 | 11/2008 | Zarins et al. |
| 2008/0281302 A1 | 11/2008 | Murphy et al. |
| 2008/0281350 A1 | 11/2008 | Sepetka et al. |
| 2008/0281393 A1 | 11/2008 | Armstrong et al. |
| 2008/0281397 A1 | 11/2008 | Killion et al. |
| 2008/0281403 A1 | 11/2008 | Kavteladze |
| 2008/0306503 A1 | 12/2008 | Que et al. |
| 2008/0306504 A1 | 12/2008 | Win et al. |
| 2008/0312732 A1 | 12/2008 | Hartley et al. |
| 2008/0319525 A1 | 12/2008 | Tieu et al. |
| 2008/0319533 A1 | 12/2008 | Lehe |
| 2009/0018633 A1 | 1/2009 | Lindquist et al. |
| 2009/0018634 A1 | 1/2009 | State |
| 2009/0018640 A1 | 1/2009 | State |
| 2009/0024157 A1 | 1/2009 | Anukhin |
| 2009/0025820 A1 | 1/2009 | Adams |
| 2009/0030502 A1 | 1/2009 | Sun et al. |
| 2009/0036968 A1 | 2/2009 | Hepworth et al. |
| 2009/0036977 A1 | 2/2009 | Rassat et al. |
| 2009/0062726 A1 | 3/2009 | Ford et al. |
| 2009/0062773 A1 | 3/2009 | Cornish et al. |
| 2009/0062834 A1 | 3/2009 | Moftakhar et al. |
| 2009/0068097 A1 | 3/2009 | Sevrain |
| 2009/0069828 A1 | 3/2009 | Martin et al. |
| 2009/0069836 A1 | 3/2009 | Labdag et al. |
| 2009/0076450 A1 | 3/2009 | Caizza et al. |
| 2009/0082800 A1 | 3/2009 | Janardhan |
| 2009/0093822 A1 | 4/2009 | Ducharme |
| 2009/0105644 A1 | 4/2009 | Leonard et al. |
| 2009/0105722 A1 | 4/2009 | Fulkerson |
| 2009/0105747 A1 | 4/2009 | Chanduszko et al. |
| 2009/0125053 A1 | 5/2009 | Ferrera et al. |
| 2009/0192455 A1 | 7/2009 | Ferrera et al. |
| 2009/0292297 A1 | 11/2009 | Ferrera |
| 2009/0299393 A1 | 12/2009 | Martin et al. |
| 2010/0022951 A1 | 1/2010 | Ferrera et al. |
| 2010/0100106 A1 | 4/2010 | Ferrera |
| 2010/0114017 A1 | 5/2010 | Lenker et al. |
| 2010/0114135 A1 | 5/2010 | Wilson et al. |
| 2010/0137892 A1 | 6/2010 | Krolik et al. |
| 2010/0152766 A1 | 6/2010 | Dieck et al. |
| 2010/0174309 A1 | 7/2010 | Fulkerson et al. |
| 2010/0217187 A1 | 8/2010 | Fulkerson et al. |
| 2010/0256600 A1 | 10/2010 | Ferrera |
| 2010/0299911 A1 | 12/2010 | Gianotti et al. |
| 2010/0318097 A1 | 12/2010 | Ferrera et al. |
| 2011/0009875 A1 | 1/2011 | Grandfield |
| 2011/0009941 A1 | 1/2011 | Grandfield et al. |
| 2011/0060212 A1 | 3/2011 | Slee et al. |
| 2011/0152920 A1 | 6/2011 | Eckhouse et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0172699 A1 | 7/2011 | Miller et al. |
| 2011/0184456 A1 | 7/2011 | Grandfield et al. |
| 2011/0190797 A1 | 8/2011 | Fulkerson et al. |
| 2011/0202088 A1 | 8/2011 | Eckhouse et al. |
| 2011/0238106 A1 | 9/2011 | Ferrera et al. |
| 2011/0270178 A1 | 11/2011 | Fiorella et al. |
| 2011/0288572 A1 | 11/2011 | Martin |
| 2011/0301686 A1 | 12/2011 | Bowman et al. |
| 2011/0319917 A1 | 12/2011 | Ferrera et al. |
| 2012/0016396 A1 | 1/2012 | Dehnad |
| 2012/0016406 A1 | 1/2012 | Ferrera et al. |
| 2012/0022576 A1 | 1/2012 | Ferrera et al. |
| 2012/0022581 A1 | 1/2012 | Wilson et al. |
| 2012/0035648 A1 | 2/2012 | Wilson et al. |
| 2012/0041411 A1 | 2/2012 | Horton |
| 2012/0041449 A1 | 2/2012 | Eckhouse |
| 2012/0041459 A1 | 2/2012 | Fiorella et al. |
| 2012/0041460 A1 | 2/2012 | Ferrera et al. |
| 2012/0041464 A1 | 2/2012 | Monetti et al. |
| 2012/0041474 A1 | 2/2012 | Eckhouse et al. |
| 2012/0041475 A1 | 2/2012 | Ferrera et al. |
| 2012/0046686 A1 | 2/2012 | Wilson et al. |
| 2012/0065660 A1 | 3/2012 | Ferrera et al. |
| 2012/0071964 A1 | 3/2012 | Cattaneo et al. |
| 2012/0078140 A1 | 3/2012 | Nita |
| 2012/0078285 A1 | 3/2012 | Griffin |
| 2012/0089216 A1 | 4/2012 | Rapaport |
| 2012/0116443 A1 | 5/2012 | Ferrera et al. |

FOREIGN PATENT DOCUMENTS

| | | |
|---|---|---|
| EP | 1000590 | 5/2000 |
| EP | 1437097 | 7/2004 |
| EP | 2257248 | 10/2011 |
| EP | 2301450 | 11/2011 |
| EP | 2417919 | 2/2012 |
| JP | 2003-033359 A | 2/2003 |
| JP | 2006-094876 | 4/2006 |
| JP | 2007-222658 A | 9/2007 |
| JP | 2007-236471 A | 9/2007 |
| WO | WO-94/03127 A1 | 2/1994 |
| WO | WO98/55173 | 12/1998 |
| WO | WO00/32265 | 6/2000 |
| WO | WO00/53120 | 9/2000 |
| WO | WO01/08743 | 2/2001 |
| WO | WO01/36034 | 5/2001 |
| WO | WO01/45569 | 6/2001 |
| WO | WO03/011188 | 2/2003 |
| WO | WO03/017823 | 3/2003 |
| WO | WO 2007/089897 | 8/2007 |
| WO | WO2007/121005 | 10/2007 |
| WO | WO 2008/117256 A2 | 10/2008 |
| WO | WO 2008/117257 A2 | 10/2008 |
| WO | WO-2008/124728 | 10/2008 |
| WO | WO2009/105710 | 8/2009 |
| WO | WO 2009/124288 | 10/2009 |
| WO | WO 2009/126747 | 10/2009 |
| WO | WO2010/010545 | 1/2010 |
| WO | WO2010/023671 | 3/2010 |
| WO | WO2010/046897 | 4/2010 |

(56) References Cited

FOREIGN PATENT DOCUMENTS

| WO | WO2010/049121 | 5/2010 |
|----|---------------|--------|
| WO | WO2010/062363 | 6/2010 |
| WO | WO2010/102307 | 9/2010 |
| WO | WO2010/115642 | 10/2010 |
| WO | WO2010/121037 | 10/2010 |
| WO | WO2010/121049 | 10/2010 |
| WO | WO2011/054531 | 5/2011 |
| WO | WO2011/095352 | 8/2011 |
| WO | WO2011/133486 | 10/2011 |
| WO | WO2011/135556 | 11/2011 |
| WO | WO2011/144336 | 11/2011 |
| WO | WO2011/147567 | 12/2011 |
| WO | WO2012/009675 | 1/2012 |
| WO | WO2012/025245 | 3/2012 |
| WO | WO2012/025247 | 3/2012 |

OTHER PUBLICATIONS

Micro Therapeutics, Inc., DBA EV3 Neurovascular, Inc., Fully deployable. Completely retrievable. Solitaire AB, Neurovascular Remodeling Device.

Robertson, Kathy, Stroke device startup lands National Science Foundation grant, Sacramento Business Journal, Oct. 23, 2009, Sacramento, California, USA.

Michael E. Kelly, MD, et al., Recanalization of an Acute Middle Cerebral Artery Occlusion Using a Self-Expanding, Reconstrainable, Intracranial Microstent as a Temporary Endovascular Bypass; American Heart Association Journal, Jun. 2008 edition, U.S.

Middle Cerebral Artery Stenting for Acute Ischemic Stroke After Unsuccessful Merci Retrieval; Special Technical Report; Neurosurgery 60:701-706, 2007.

David M. Pelz, et al., Advances in Interventional Neuroradiology 2007; American Heart Association Journal, Nov. 2007 edition. U.S.

Philippa C. Lavallée, et al., Stent-Assisted Endovascular Thrombolysis Versus Intravenous Thrombolysis Versus Intravenous Thrombolysis in Internal Carotid Artery Dissection with Tandem Internal Carotid and Middle Cerebral Artery Occlusion. AHA 2007.

E.I. Levy et al., Self-Expanding Stents for Recanalization of Acute Cerebrovascular Occlusions ; AJNR May 28, 2007 U.S.

T.W. Duerig, D.E. Tolomeo, M. Wholey, An Overview of Superelastic Stent Design.

Henkes, H. et al., "A Microcatheter-Delivered Highly-Flexible and Fully-Retrievable Stent, Specifically Designed for Intracranial Use," *Interventional Neuroradiology*, vol. 9, pp. 391-393 (Dec. 2003).

Doerfler, A. et al., "A Novel Flexible, Retrievable Endovascular Stent System for Small-Vessel Anatomy: Preliminary *In Vivo* Data," *Am. J. Neuroradiol.* vol. 26, pp. 862-868 (Apr. 2005).

Liebig, T. et al., "A novel self-expanding fully retrievable intracranial stent (SOLO): experience in nine procedures of stent-assisted aneurysm coil occlusion," *Neuroradiology* vol. 48, pp. 471-478 (Jul. 2006).

Yavuz, K. et al., "Immediate and midterm follow-up results of using an electrodetachable, fully retrievable SOLO stent system in the endovascular coil occlusion of wide-necked cerebral aneurysms," J. Neurosurg. vol. 107, pp. 49-55 (Jul. 2007).

"Penumbra, Inc. Enrolls First Patients in PULSE Clinical Trial to Evaluate a Fully Retrievable, Dense Mesh Temporary Stent for Immediate Flow Restoration in Interventional Acute Ischemic Stroke Treatment," Business Wire, Nov. 1, 2010, downloaded at http://www.businesswire.com/news/home/20101101006991/en/Penumbra-Enrolls-Patients-PULSE-Clinical-Trial-Evaluate.

U.S. Appl. No. 60/980,736, filed Oct. 17, 2007, Fulkerson et al.
U.S. Appl. No. 60/987,384, filed Nov. 12, 2007, Fulkerson et al.
U.S. Appl. No. 60/989,422, filed Nov. 20. 2007, Ferrera et al.
U.S. Appl. No. 61/015,154, filed Dec. 19, 2007, Ferrera et al.

Wakhloo, et al., "Retrievable Closed Cell Intracranial Stent for Foreign Body and Clot Removal," Neurosurgery, May, 2008.

Michael E. Kelly, MD, et al., Recanalization of an Acute Cerebral Artery Occlusion Using a Self-Expanding, Reconstrainable, Intracranial Microstent as a Temporary Endovascular Bypass; AHA Journal, Jun. 2008 edition.

Eric Sauvegeau, MD et al. Middle Cerebral Artery Stenting for Acute Ischemic Stroke After Unsuccessful Merci Retrieval; Special Technical Report; Neurosurgery 60:701-706, 2007.

David M. Pelz, et al., Advances in Interventional Neuroradiology 2007; American Heart Association Journal, Nov. 2007.

Philippa C. Lavallee, et al., Stent-Assisted Endovascular Thrombolysis Versus Intravenous Thrombolysis in Internal Carotid Artery Dissection with Tandem Internal Carotid and Middle Cerebral Artery Occlusion, AHA 2007.

E.I. Levy et al., Self-Expanding Stents for Recanalization of Acute Cerebrovascular Occulsions; AJNR May 28, 2007.

\* cited by examiner

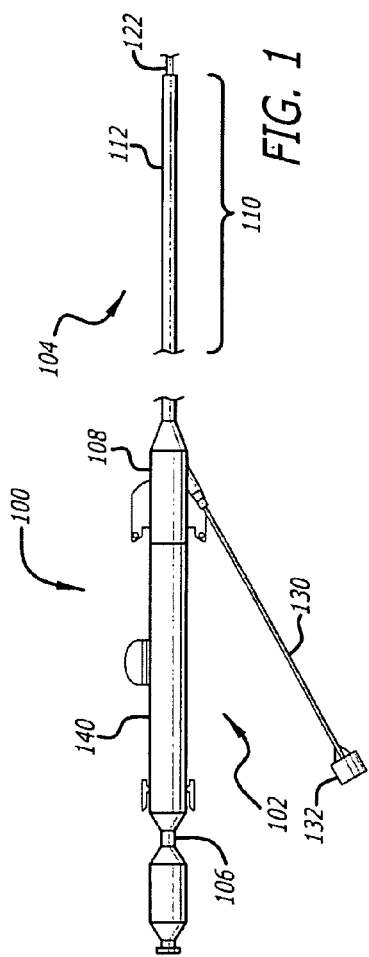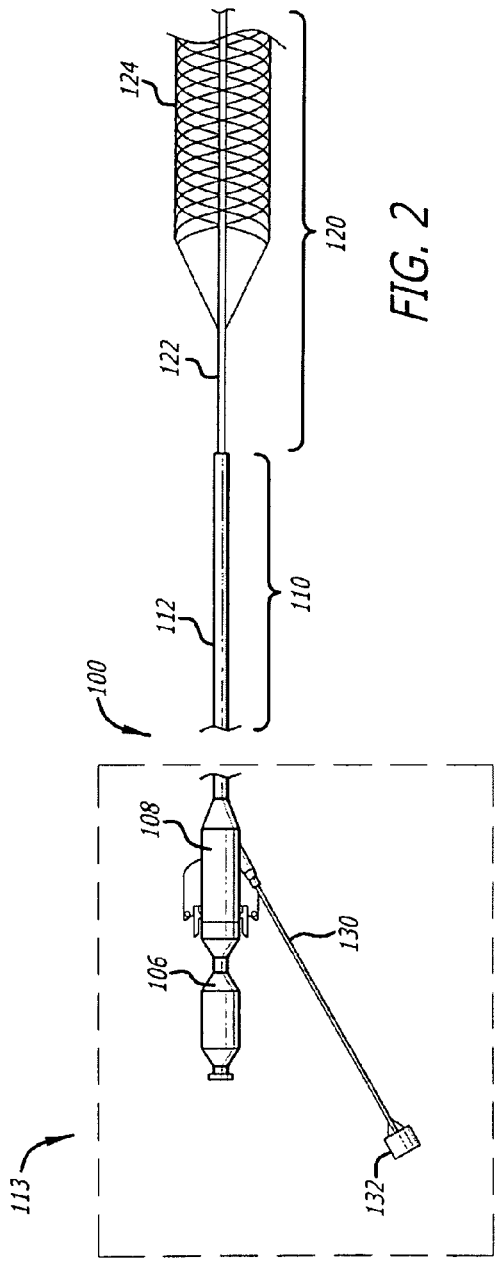

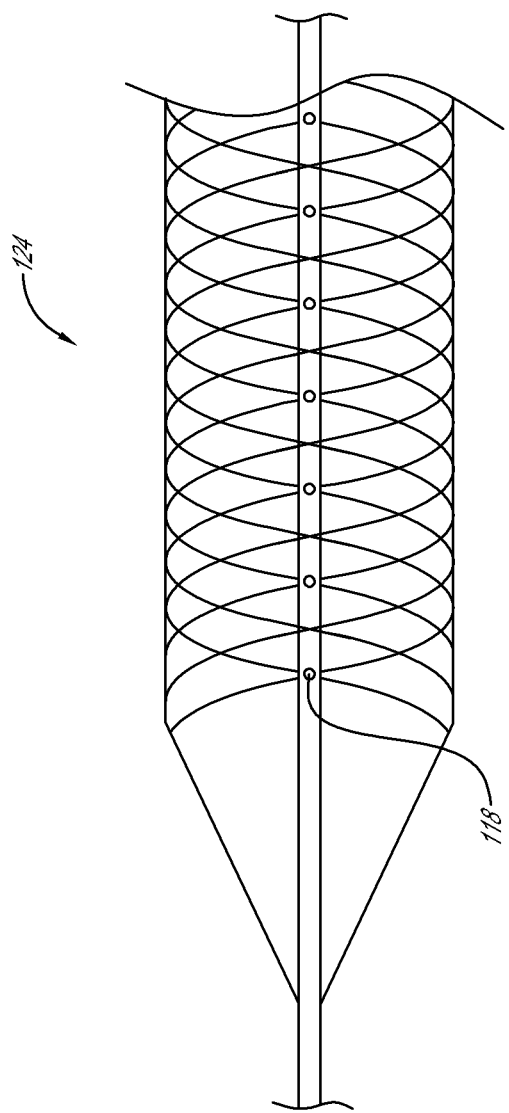

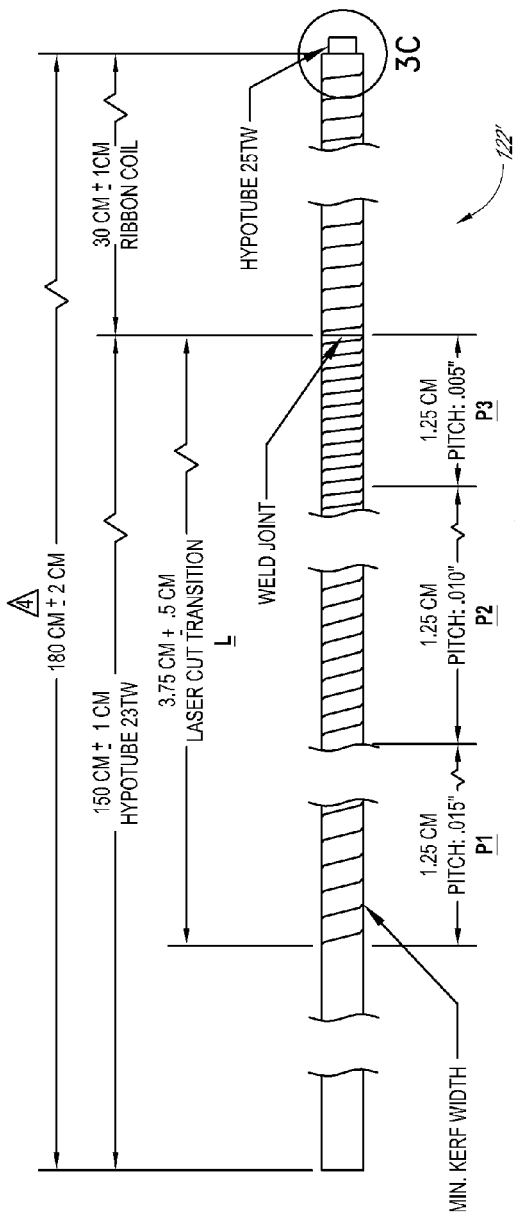
FIG. 3A
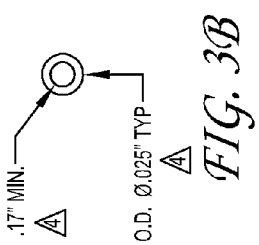
FIG. 3C
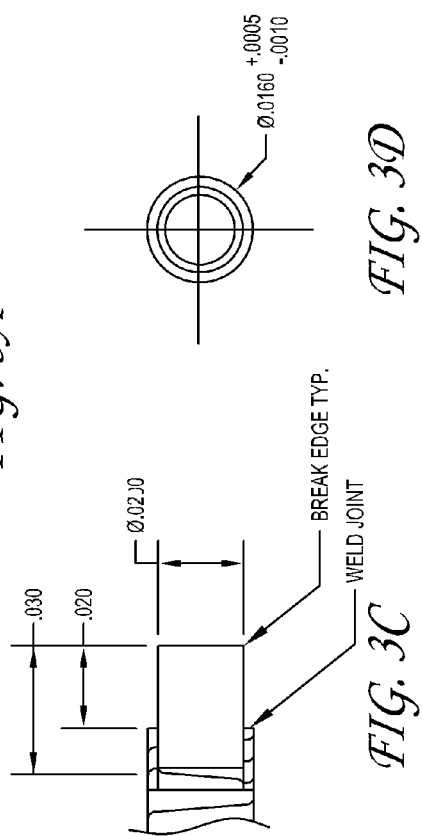
FIG. 3D
FIG. 3B

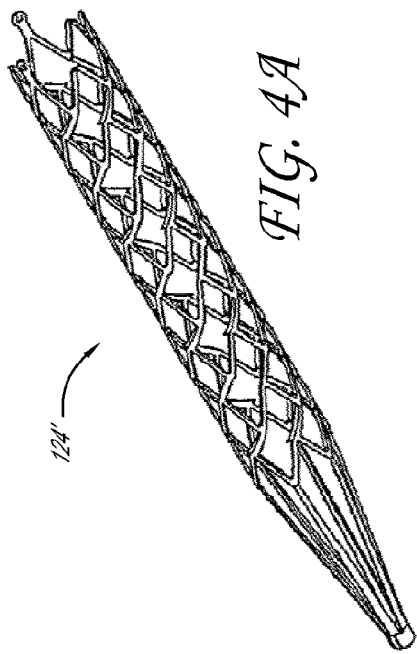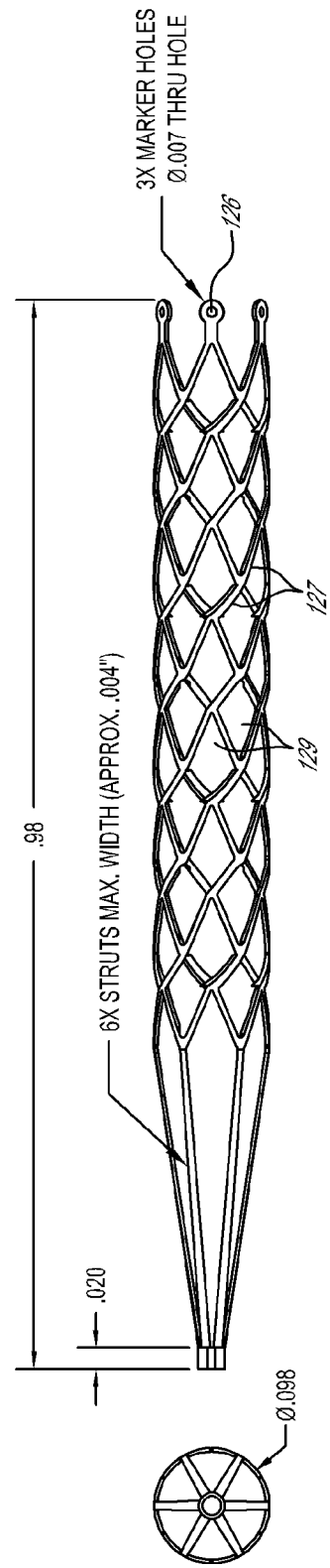

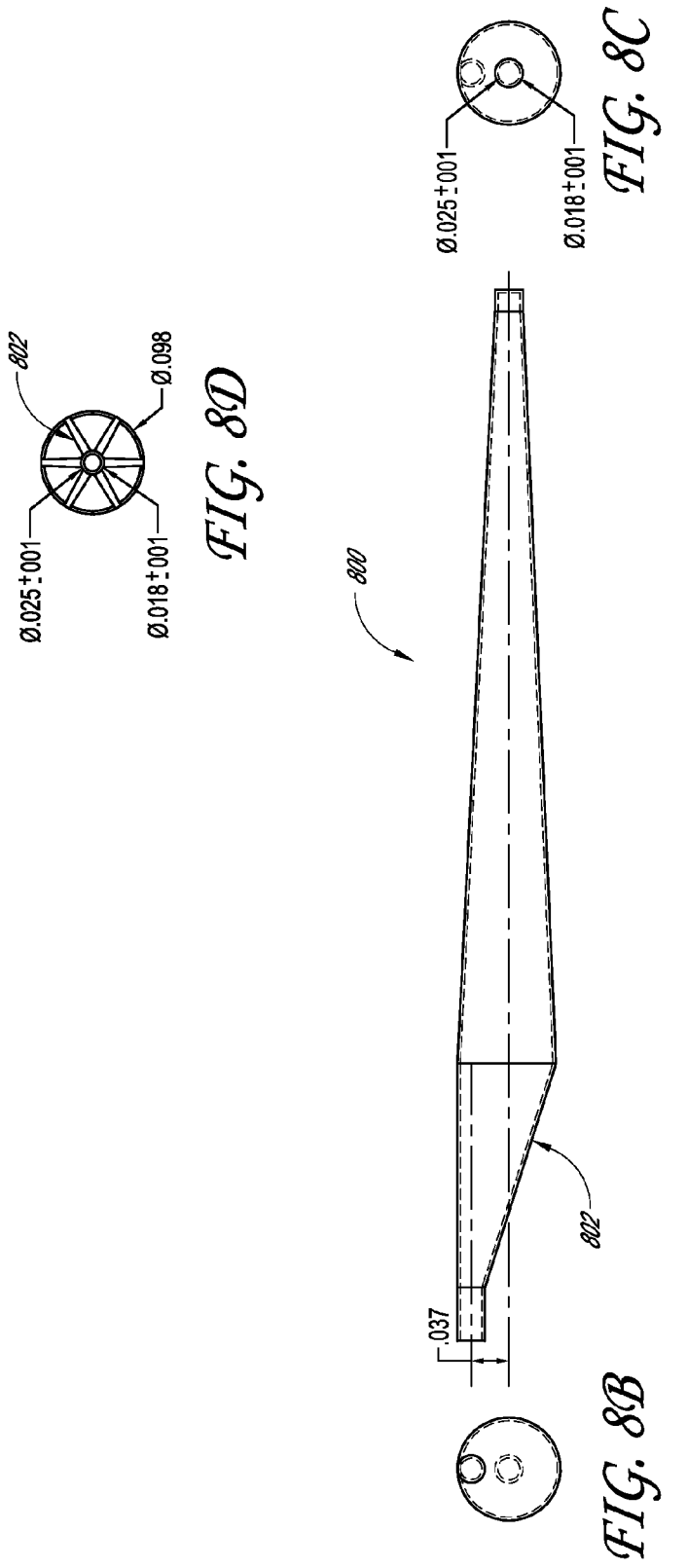

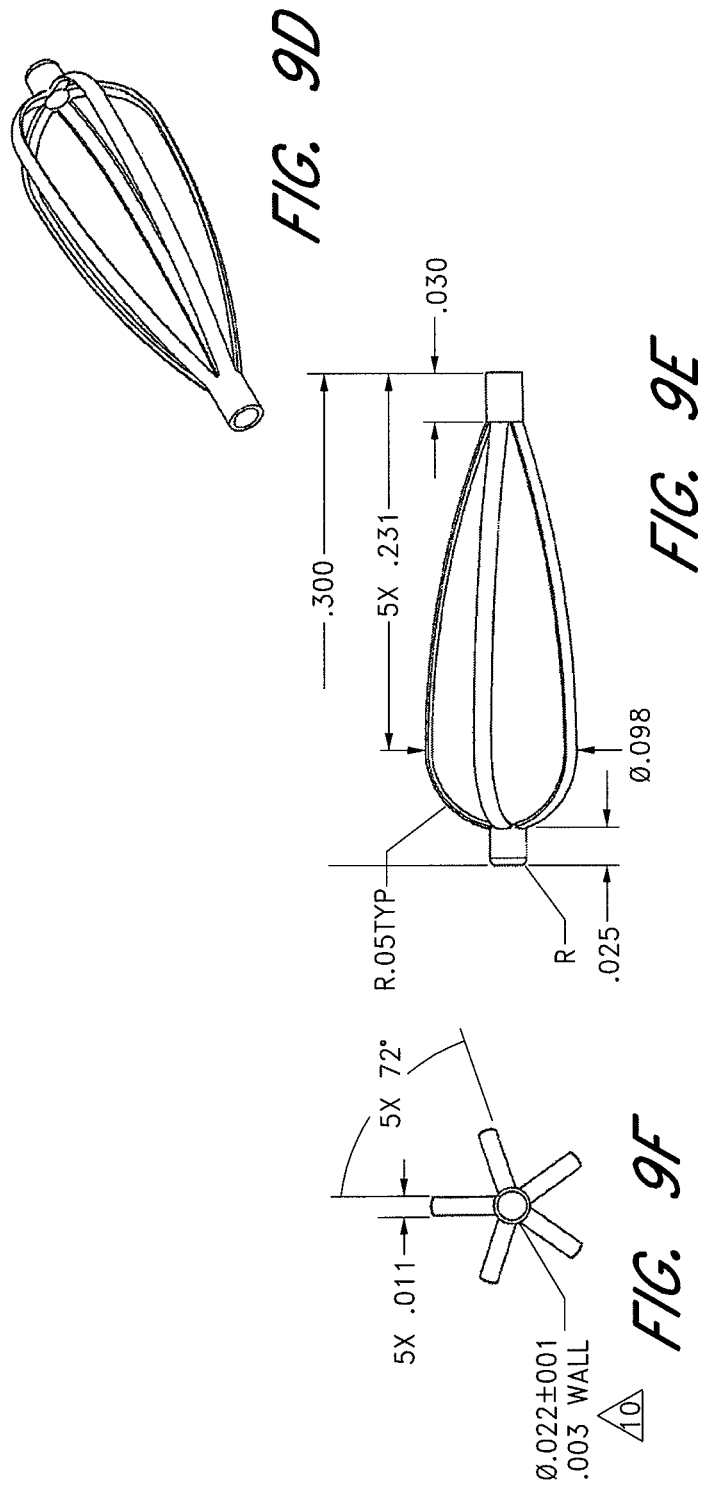

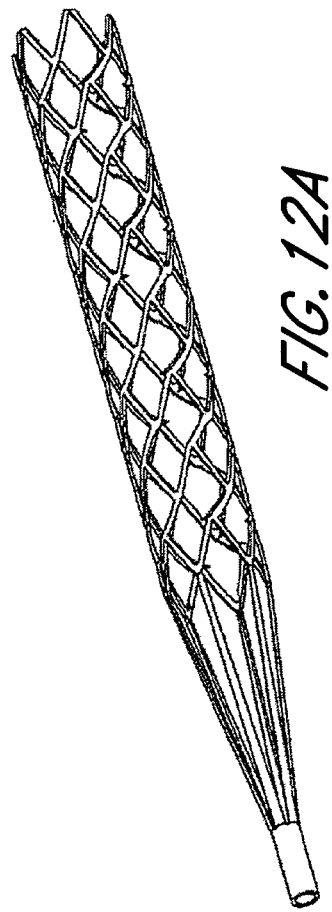
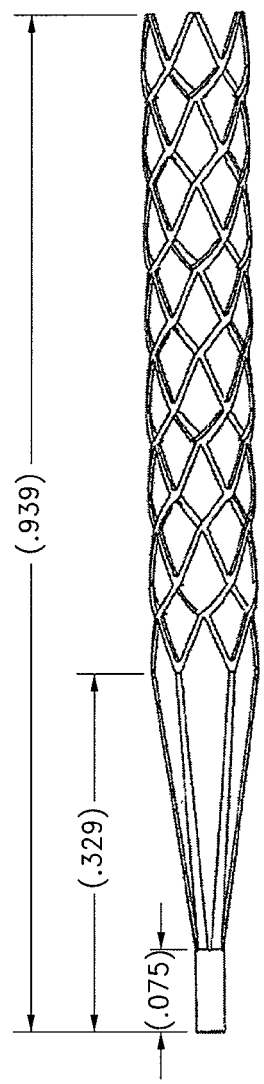
FIG. 12A
FIG. 12B

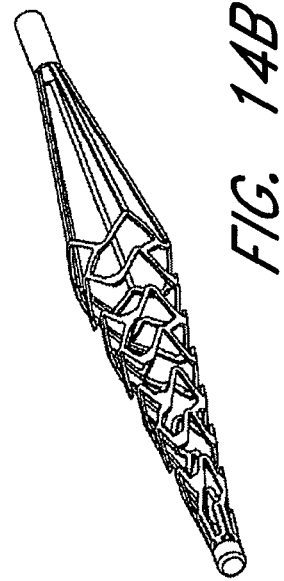
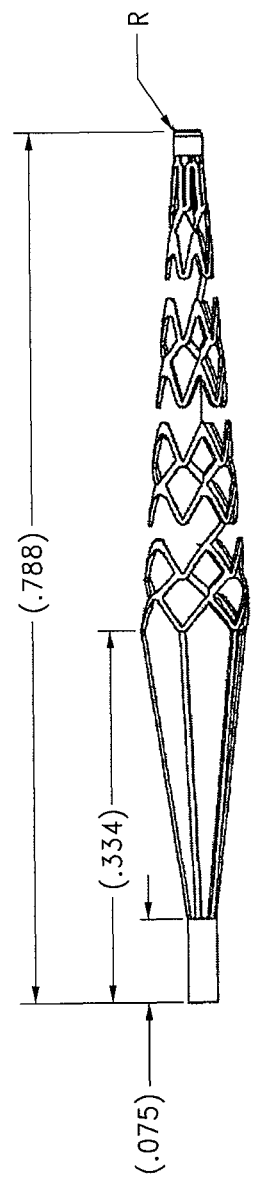

ACUTE STROKE REVASCULARIZATION/RECANALIZATION SYSTEMS PROCESSES AND PRODUCTS THEREBY

CROSS-REFERENCE TO RELATED APPLICATIONS

The instant application claims full Paris Convention priority to, and incorporates expressly by reference U.S. Provisional Application Ser. No. 60/980,736, filed Oct. 17, 2007. Likewise, the instant application claims priority to, and incorporates by reference U.S. Provisional Application Ser. No. 61/044,392, filed Apr. 11, 2008; U.S. Provisional Application Ser. No. 61/015,154, filed Dec. 19, 2007; U.S. Provisional Application Ser. No. 60/989,422, filed Nov. 20, 2007; U.S. Provisional Application Ser. No. 60/987,384, filed Nov. 12, 2007; and U.S. Provisional Application Ser. No. 61/019,506, filed Jan. 7, 2008, each as if fully set forth herein.

BACKGROUND OF THE INVENTION

The present disclosure relates to minimally invasive and catheter delivered revascularization systems for use in the vasculature, especially those suited for usage above the juncture of the Subclavian Artery and Common Carotid Artery. In particular, this disclosure relates to revascularization devices for use in treatment of ischemic stroke, including improved neurological medical devices which are tethered or reconstrainable self-expanding neurological medical devices.

SUMMARY OF THE INVENTION

According to embodiments of the present invention, there are disclosed acute stroke revascularization/recanalization systems comprising, in combination; catheter systems having guidewires to access and emplace improved neurological medical devices into the cerebral vasculature, the systems including proximal stainless steel pushers with distal nitinol devices or one-piece nitinol devices. In some embodiments, the systems comprise a polymeric liner incorporated within the pusher to improve trackability of the guidewire. In some embodiments, the polymeric liner extends beyond the distal tip of the pusher for guiding the guidewire and preventing entanglement in the nitinol device.

According to embodiments, there are disclosed one-piece nitinol devices in combination with the above disclosed and/or claimed catheter systems.

Briefly stated, according to embodiments a novel enhanced tethered revascularization device is deliverable through highly constricted and tortuous vessels, entering a zone associated with subject thrombi/emboli, where deployment impacts the embolus, compacting the same into luminal walls which enables perfusion and lysis of the embolus, while the revascularization device itself remains continuous with the delivery system acting as a filter, basket or stand alone revascularization mechanism, depending on the status of the embolus and other therapeutic aspects of the treatment being offered for consideration.

According to embodiments of the system and processes of the present invention, in certain iterations, once deployed the instant system compacts the embolus against the luminal wall, creating a channel for blood flow which may act like a natural lytic agent to lyse or dissolve the embolus.

According to embodiments, there is provided an improved neurological medical device which comprises, in combination, a catheter system effective for delivering a combination radial filter/revascularization device and basket assembly into a desired location in the cerebral vascular system, a self-expanding radial filter/revascularization device and basket assembly detachably tethered to the catheter system which functions in at least three respective modes, wherein the radial filter/revascularization device and basket assembly is attached to the catheter and wherein radial filter/revascularization device and basket assembly further comprises at least two states per mode, a retracted state and an expanded state; and wherein the radial filter/revascularization device and basket assembly may retracted into the retracted state after deployment in an expanded state, in each mode.

According to embodiments, there is provided a process comprising in combination providing a revascularization device tethered to a catheter by emplacing the system into a patient for travel to a desired location in a vessel having an obstruction/lesion and deploying the revascularization device by allowing it to move from a first state to a second state across a lesion which compresses the subject embolus into a luminal wall to which it is adjacent whereby creating a channel for blood flow as a lytic agent, and removing the system which the obstruction/lesion is addressed.

It is noted that if blood flow does not lyse the blood embolus, lytic agents can be administered via the guidewire lumen, as a feature of the present invention.

According to embodiments, there is provided a process whereby the revascularization device tethered to a catheter functions as a radial filter to prevent downstream migration of emboli.

The U.S. Food and Drug Administration (FDA) has previously approved a clot retrieval device (The Merci® brand of retriever X4, X5, X6, L4, L5 & L6: Concentric Medical, Mountain View, Calif.). Unfortunately, when used alone, this clot retriever is successful in restoring blood flow in only approximately 50% of the cases, and multiple passes with this device are often required to achieve successful recanalization. IA thrombolytics administered concomitantly enhance the procedural success of this device but may increase the risk of hemorrhagic transformation of the revascularization infarction. There have been several reports of coronary and neurostent implantation used for mechanical thrombolysis of recalcitrant occlusions. In summary, stent placement with balloon-mounted or self-expanding coronary and neuro-types of stents has been shown to be an independent predictor for recanalization of both intracranial and extra cranial cerebrovasculature occlusions. This provides some insight into approaches needed to overcome these longstanding issues.

By way of example, self-expanding stents designed specifically for the cerebro-vasculature can be delivered to target areas of intracranial stenosis with a success rate of >95% and an increased safety profile of deliverability because these stents are deployed at significantly lower pressures than balloon-mounted coronary stents. However, systems using this data have yet to become commercial, available or accepted by most practitioners.

The use of self-expanding stents is feasible in the setting of symptomatic medium—and large-vessel intracranial occlusions. With stent placement as a first-line mechanical treatment or as a "last-resort" maneuver, TIMI/TICI 2 or 3 revascularization can be successfully obtained, according to clinical data now available.

The literature likewise suggests that focal occlusions limited to a single medium or large vessel, particularly solitary occlusions of the MCA or VBA, may be preferentially amenable to stent placement and thus can help clinicians to achieve improved rates of recanalization. In addition, gender may play a role in the success of self-expanding stent implementation. However, systems need to be designed to execute on this.

Despite increasing utilization of prourokinase rt-PA (recombinant tissue plasminogen activator) or other antithrombotic agents (e.g., Alteplase® and Reteplase®), recanalization rates remain approximately 60%. The major concerns with pharmacologic thrombolysis (alone) has been the rate of hemorrhage, inability to effectively dissolve fibrin\platelet-rich clots, lengthy times to recanalization, and inability to prevent abrupt reocclusions at the initial site of obstruction. In PROACTII, ICH with neurologic deterioration within 24 hours occurred in 10.9% of the prourokinase group and 3.1% of the control group (P=0.06), without differences in mortality. Abrupt reocclusions or recanalized arteries has been found to occur relatively frequently, even with the addition of angioplasty or snare manipulation for mechanical disruption of thrombus, and seems to be associated with poor clinical outcomes.

The use of other mechanical means has been reported to be effective in recanalization of acute occlusions. It makes sense that a combination of mechanical and pharmacologic approaches would yield greater benefit.

A known investigation in an animal model has shown, both the Wingspan® brand of self-expanding stent and Liberte® brand of balloon-mounted stent (Boston Scientific, Boston, Mass.) were able to re-establish flow through acutely occluded vessels. The self-expanding stents performed better than the balloon-mounted stents in terms of navigability to the target site. The self-expanding stents incurred lower rates of vasospasm and side-branch occlusions, which suggests superiority of these stents, over balloon-mounted stents, to maintain branch vessel patency during treatment of acute vessel occlusion. In previous animal studies conducted, intimal proliferation and loss of lumen diameter were seen after the implantation of bare-metal, balloon-expandable stents. The literature further supports this set of issues.

These phenomena are believed to be attributable to intimal injury created during the high-pressure balloon angioplasty that is required for stent deployment.

Compared with coronary balloon-mounted stents, self-expanding stents designed for use in the intracranial circulation are superior because they are easier to track to the intracranial circulation and safer to deploy in vessels in which the true diameter and degree of intracranial atherosclerotic disease are unclear.

Moreover, based on previous experience, currently available self-expanding stents provide enough radial outward force at body temperature to revascularize occluded vessels, with low potential for the negative remodeling and in-stent restenosis that are associated with balloon-mounted stents in nonintracranial vascular beds.

Because self-expanding stents are not mounted on balloons, they are the most trackable of the stents currently available for the intracranial circulation. Unlike clot retrievers, which lose access to the target (occlusion site) every time they are retrieved (and often to necessitate multiple passes), self-expanding stents allow for wire access to the occlusion at all times, increasing the safety profile of the procedure by not requiring repeat maneuvers to gain access to the target site (as in the case for the Merci® brand of clot retriever).

Self-expanding stent placement of acute intracranial vessel occlusions may provide a novel means of recanalization after failure of clot retrieval, angioplasty, and/or thrombolytic therapy. The patency rates in this series are encouraging, yet issues remain to be addressed.

In the setting of acute stroke, restoring flow is of singular importance. In-stent stenosis or delayed stenosis may be treated in a delayed fashion on an elective basis, should the patient achieve a functional recovery from the stroke.

Recanalization with self-expanding stents may provide flow through the patent artery, and restore flow to the perforators, or, alternatively, they may remain occluded. Restoring flow to the main artery, however, will reduce the stroke burden. What is needed is a solution leveraging positive aspects of stent-based treatment without the negative outcomes which have been associated with traditional stenting.

DRAWINGS OF THE INVENTION

The above-mentioned features and objects of the present disclosure will become more apparent with reference to the following description taken in conjunction with the accompanying drawings wherein like reference numerals denote like elements and in which:

FIG. 1 is a perspective view of an embodiment of an acute stroke recanalization system according to embodiments of the present disclosure in a first configuration; and FIG. 2 is a perspective view of an embodiment of an acute stroke recanalization system according to embodiments of the present disclosure tailored for use with the neurovasculature in a second configuration, further illustrating modular aspects of the system as used with tethered or reconstrainable self-expanding neurological medical devices.

FIG. 2A illustrates a detailed view of the inner catheter of FIG. 2.

FIGS. 3A-3D illustrate an embodiment of an inner catheter of the acute stroke recanalization system of FIGS. 1 and 2.

FIGS. 4A-4C illustrate a perspective view, a side view, and a front view, respectively, of an embodiment of a self-expanding revascularization device.

Figure 7:
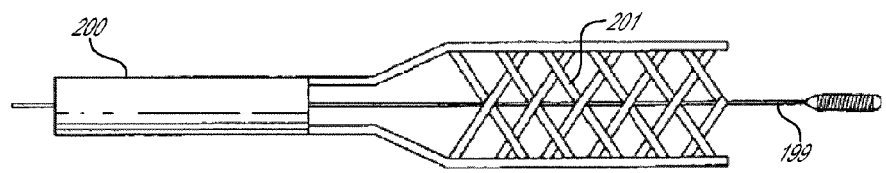
Figure 9A:
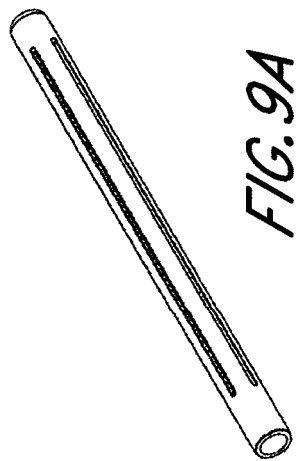
Figure 9B:
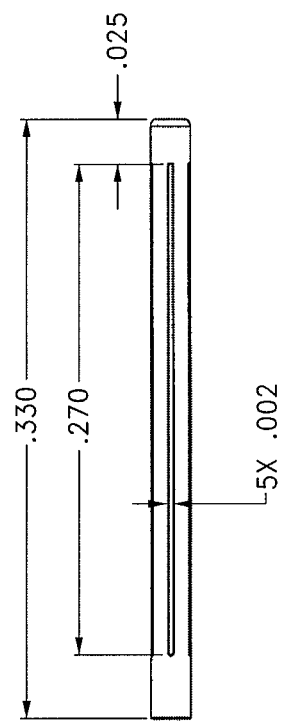
Figure 9C:
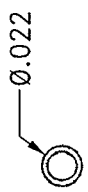
Figure 10A:
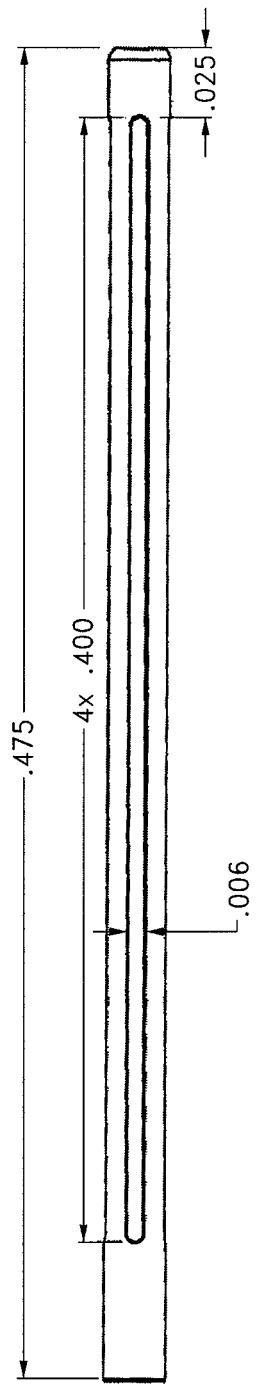
Figure 10B:
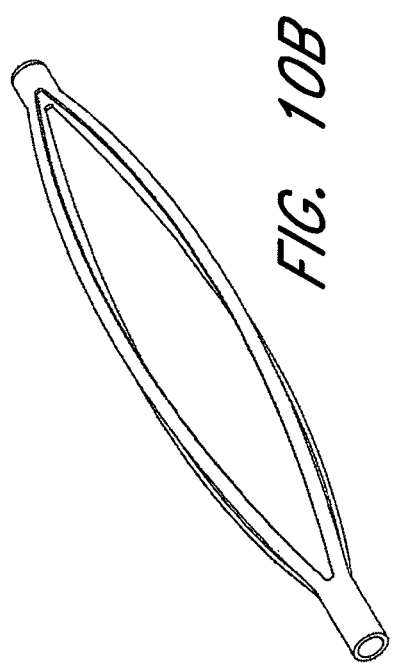
Figure 10C:
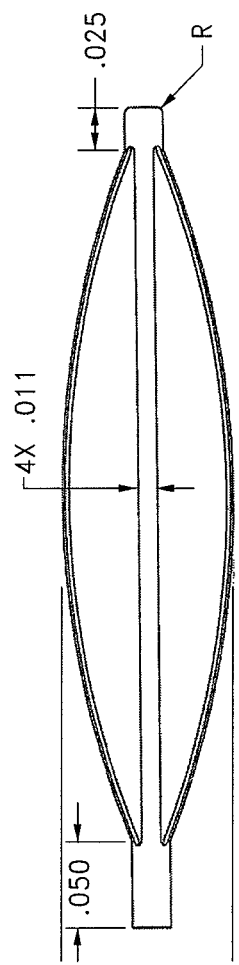
Figure 11A:
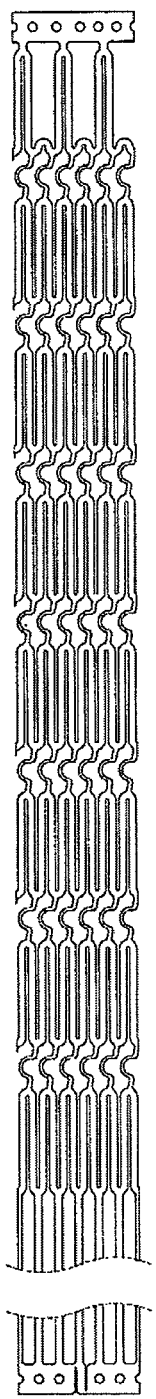
Figure 11B:
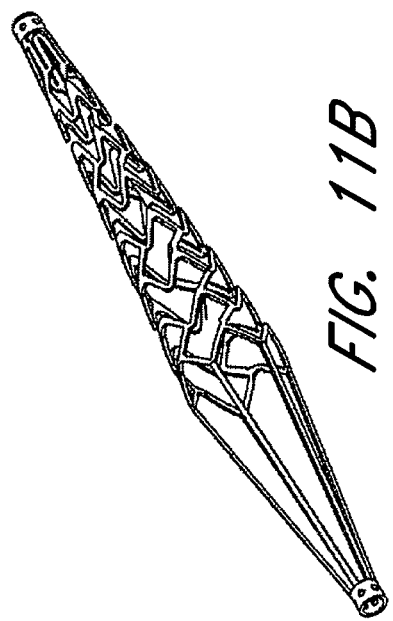
Figure 11C:
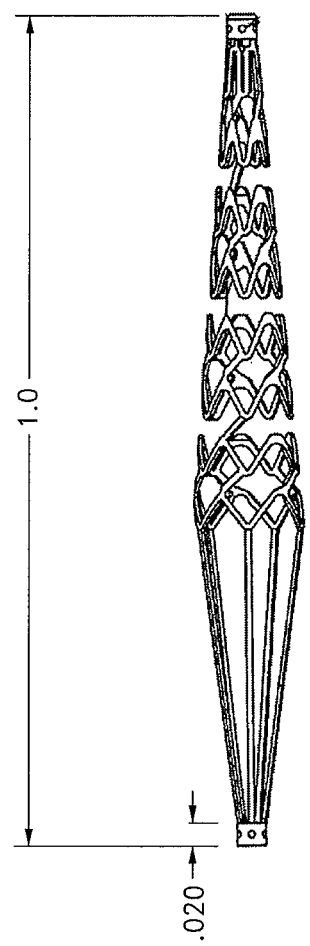
Figure 11D:
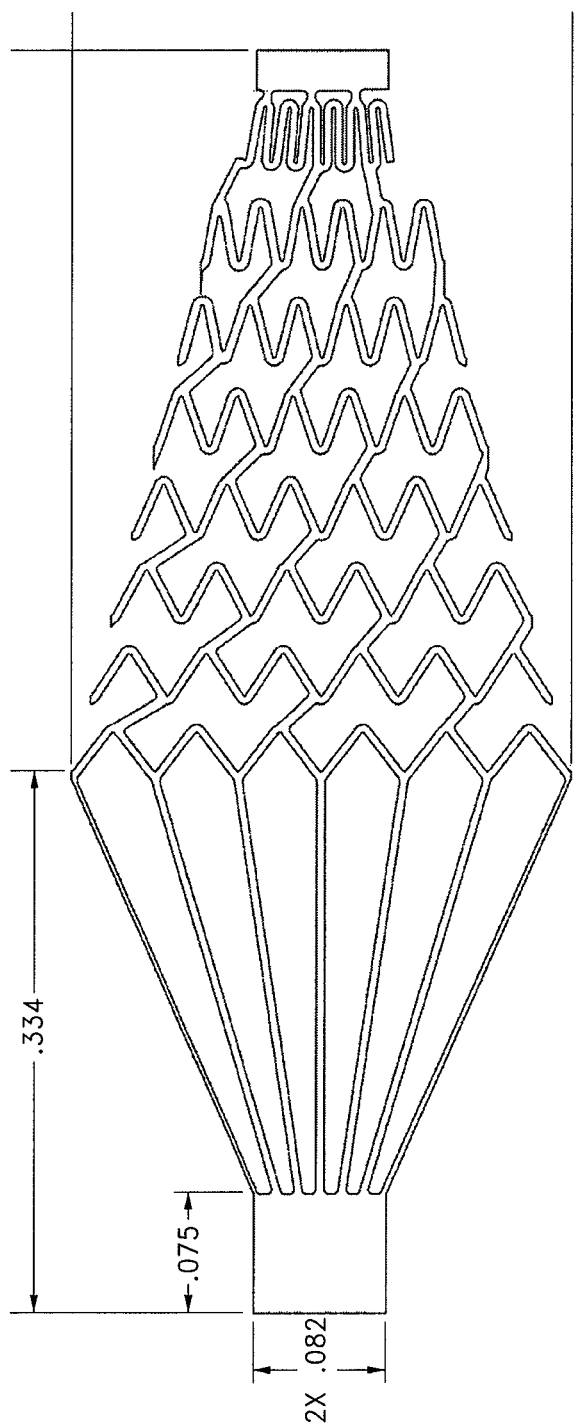
Figure 12C:
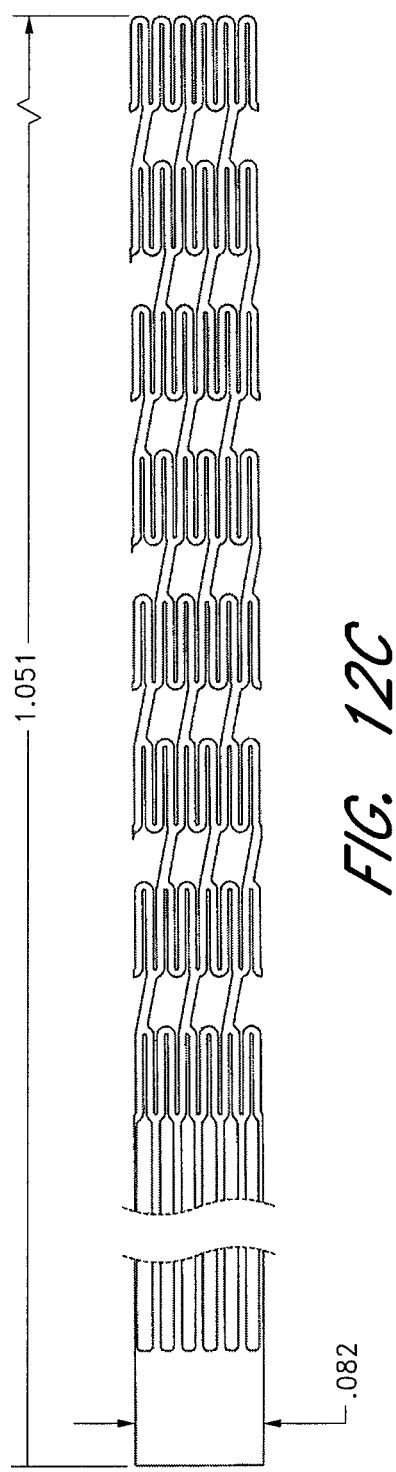
Figure 12D:
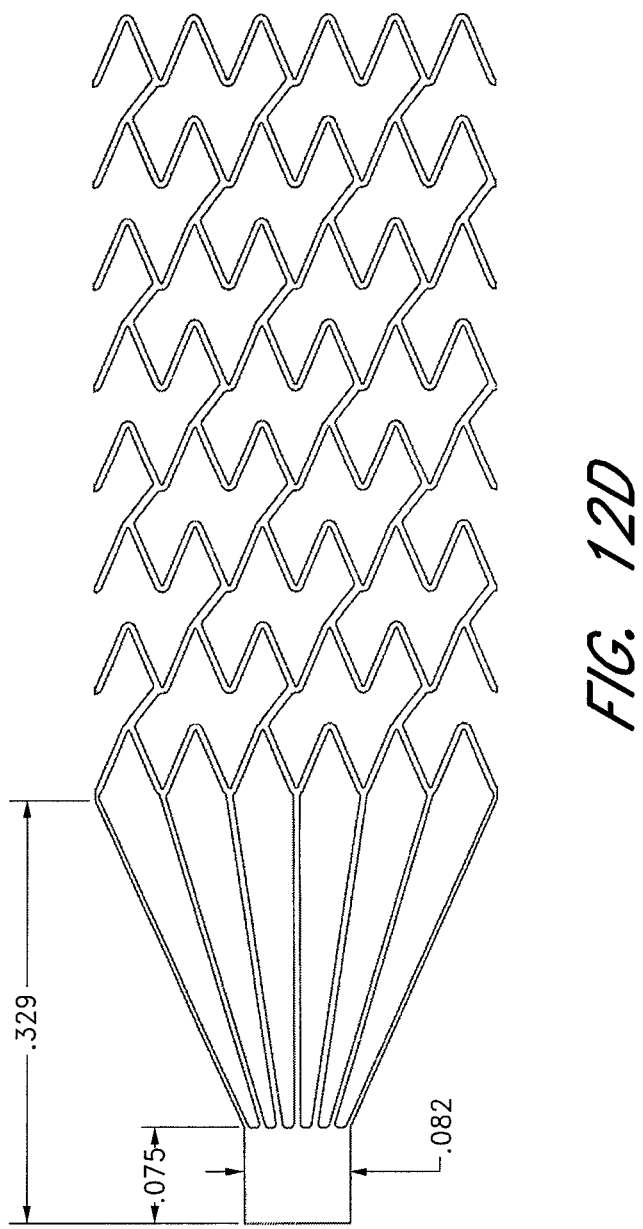
Figure 13A:
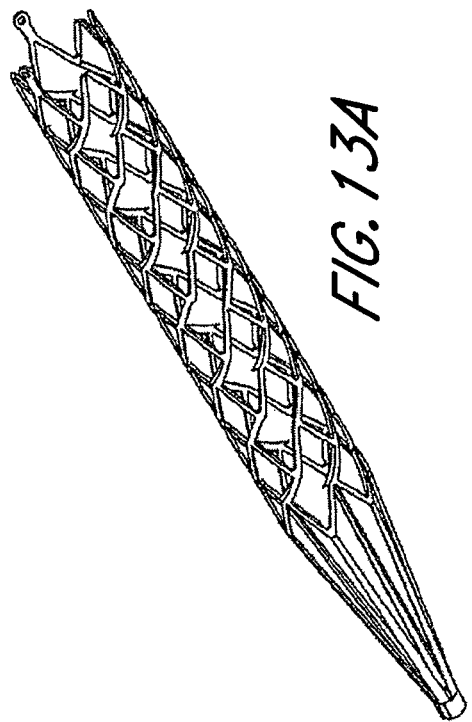
Figure 13B:
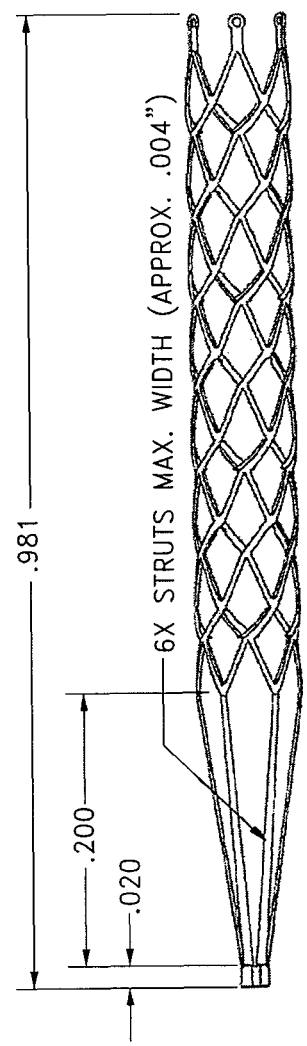
Figure 13C:
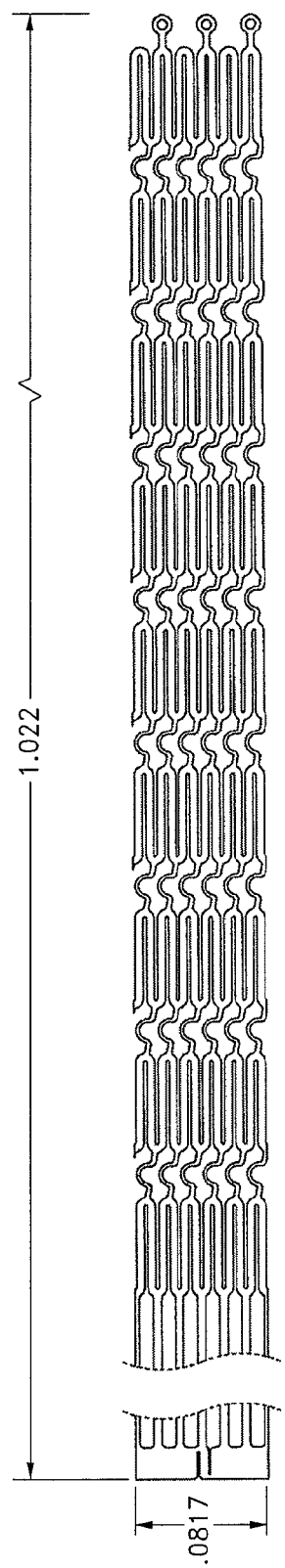
Figure 14A:
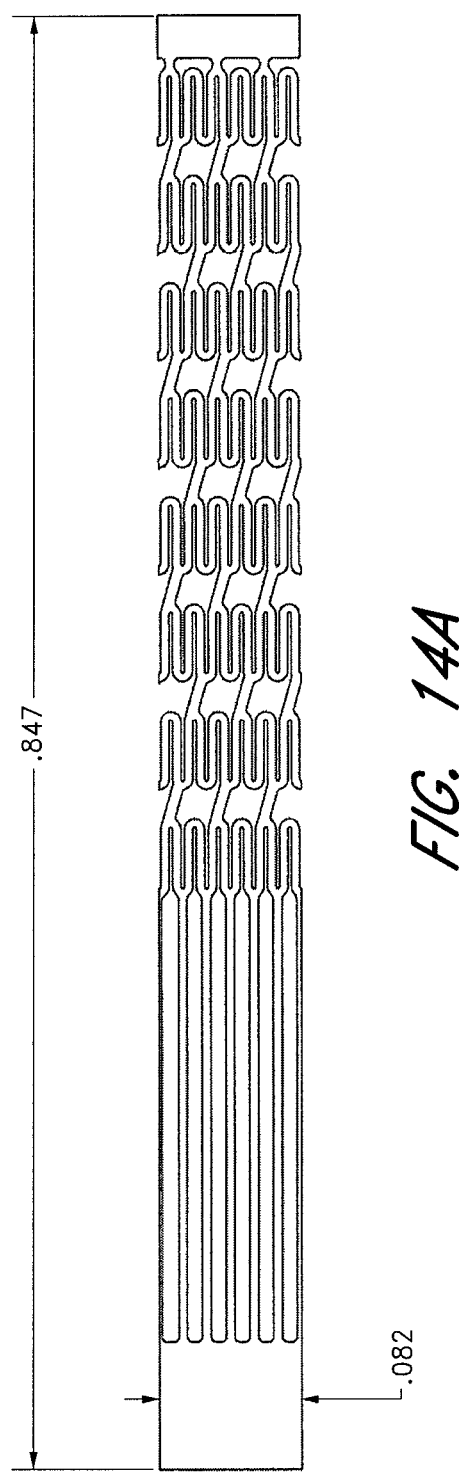
Figure 15:
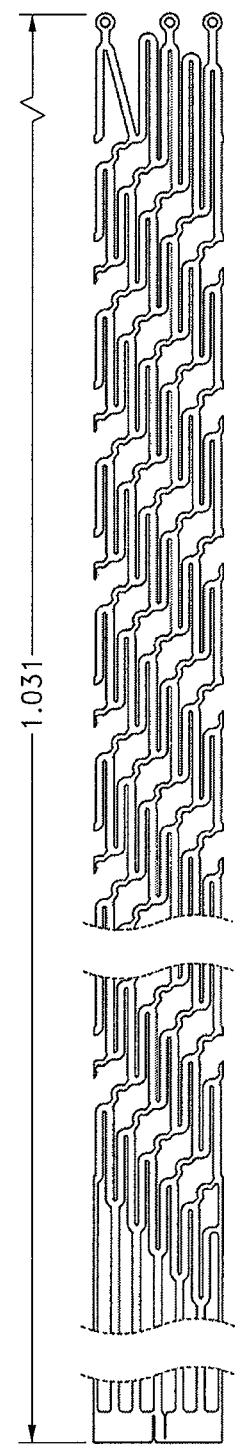
Figure 16:
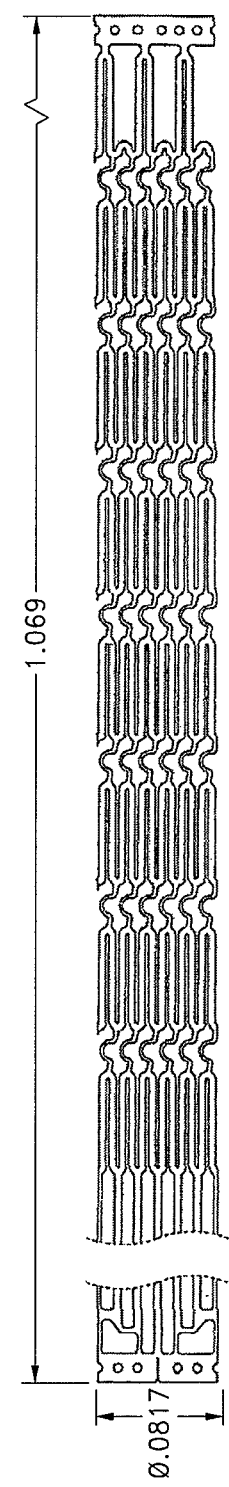
Figure 17A:
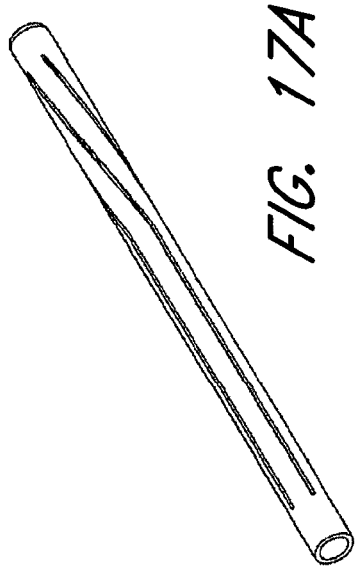
Figure 17B:
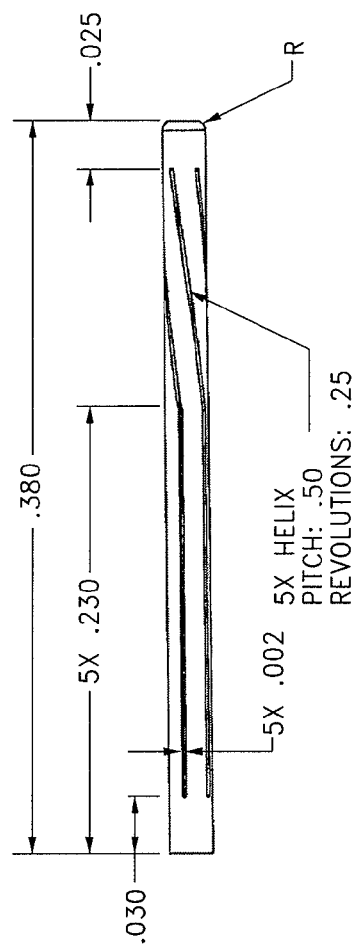
Figure 17C:
Figure 17D:
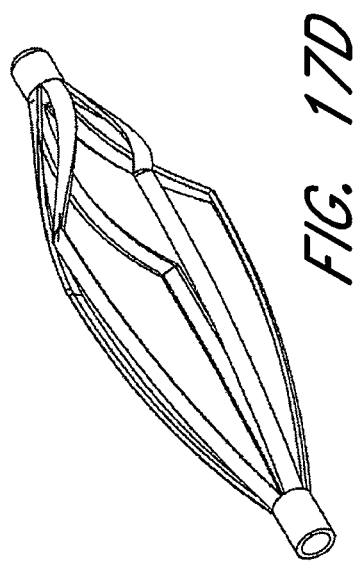
Figure 17E:
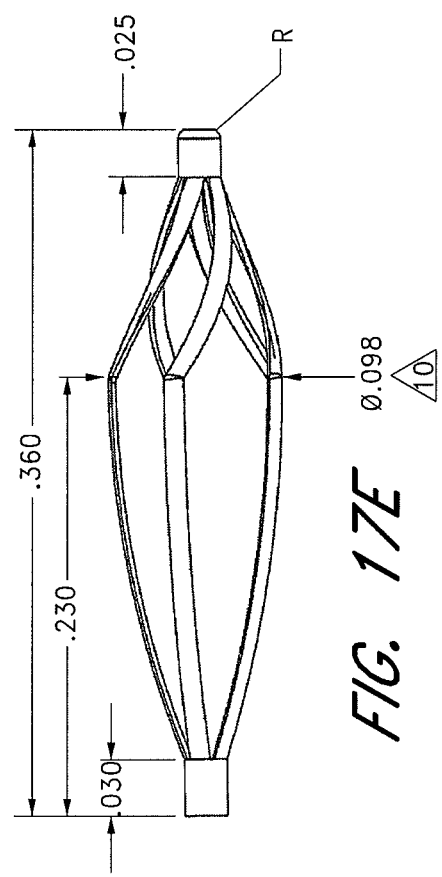
Figure 17F:
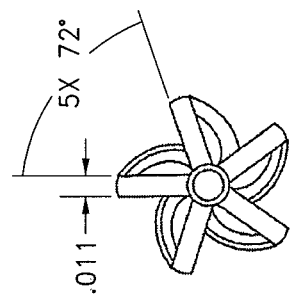

FIG. 7 likewise schematically depicts a delivery system with embodiments of a tethered stent for use with an over-the wire guidewire system.

FIGS. 8A-8D illustrate an embodiment of a revascularization device configured for eccentric coupling to a pusher.

FIGS. 9A-9F, 10A-10C, 11A-11D, 12A-12D, 13A-13C, 14A-14C, 15, 16, and 17A-17F illustrate various embodiments of revascularization devices.

Figure 18A:
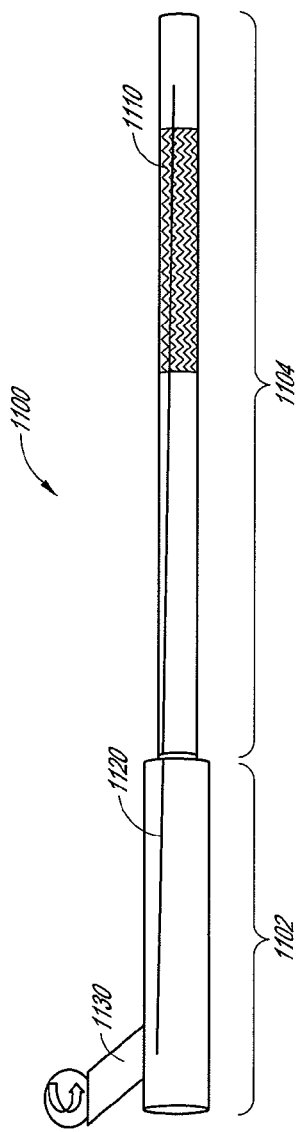
Figure 18B:
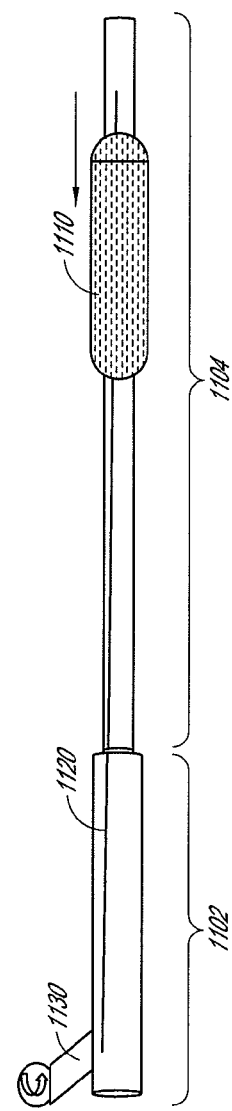

FIGS. 18A and 18B are perspective views of an embodiment of a rapid reperfusion device of the present disclosure.

Figure 19A:
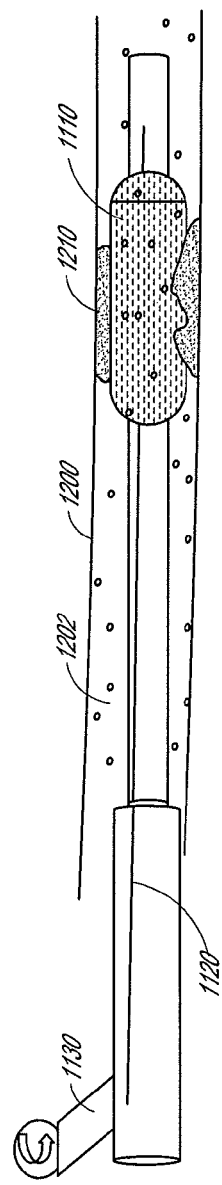
Figure 19B:
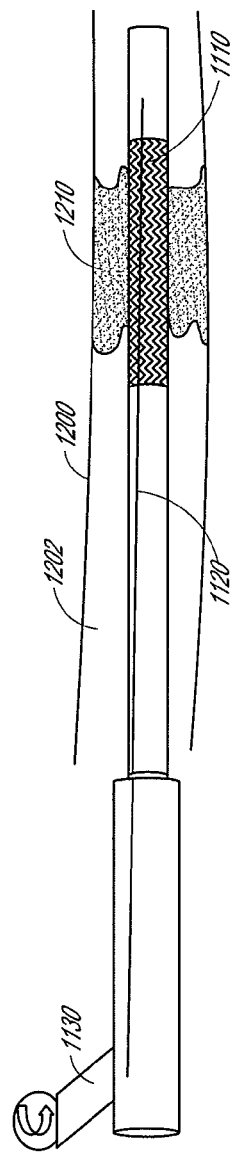

FIGS. 19A and 19B are perspective views of an embodiment of a method for use of a rapid reperfusion device of the present disclosure.

Figure 20A:
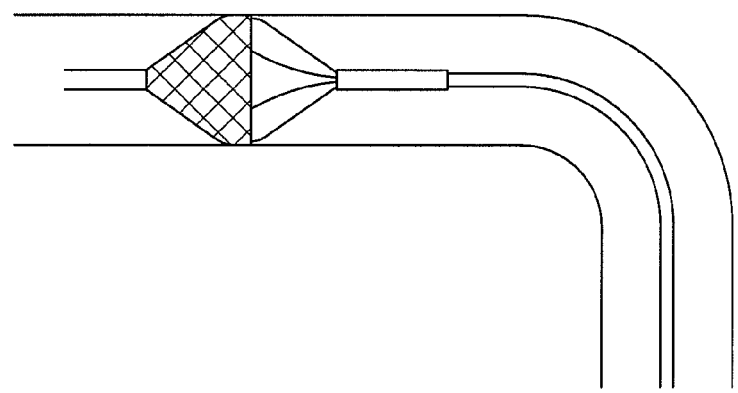

FIG. 20A is a side view of an embodiment of a rapid reperfusion device comprising an infusable microwire with an integrated filter.

Figure 20B:
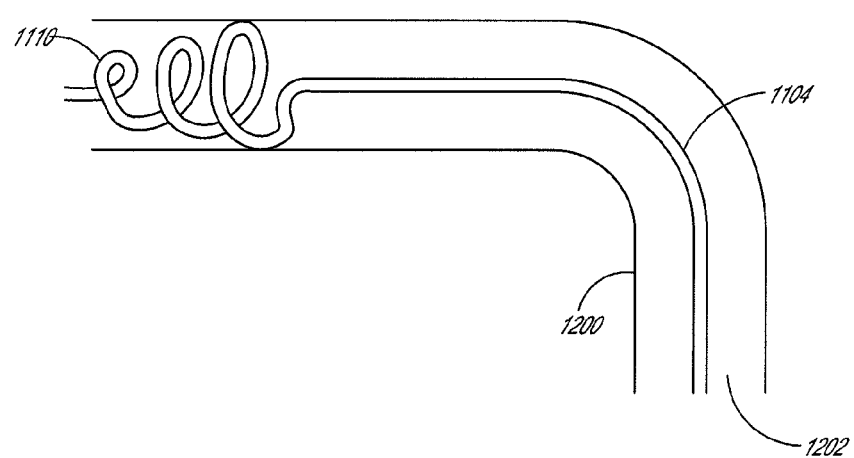

FIG. 20B is a side view of an embodiment of a rapid reperfusion device comprising an infusable coil.

Figure 21A:
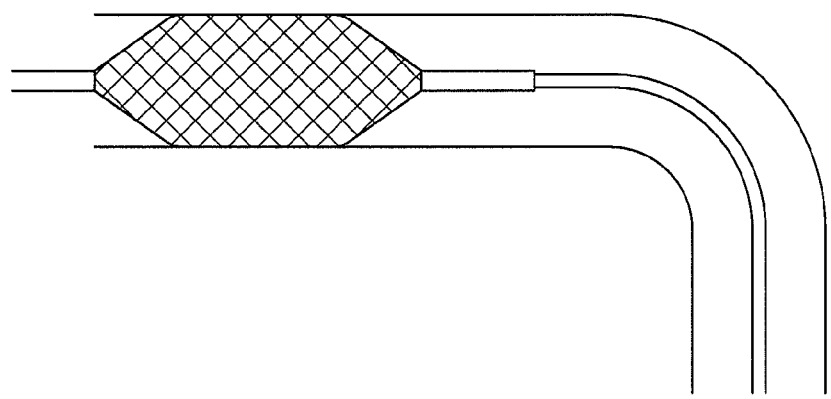

FIG. 21A is a side view of an embodiment of a rapid reperfusion device comprising an infusable temporary stent.

Figure 21B:
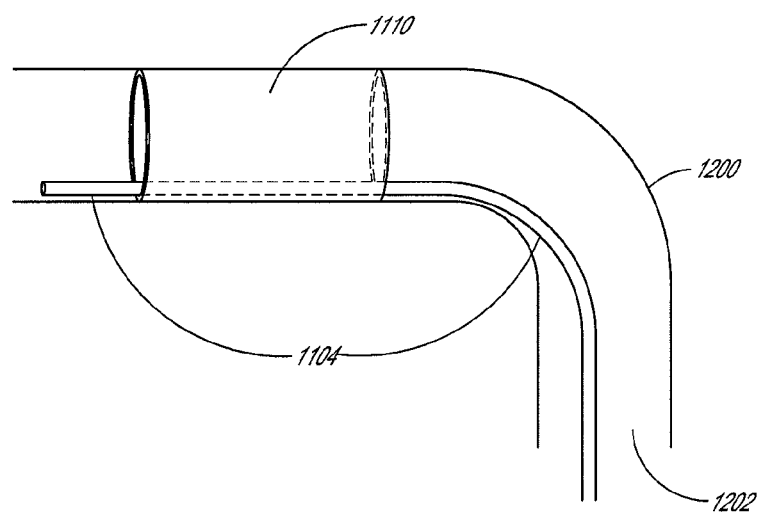

FIG. 21B is a side view of an embodiment of a rapid reperfusion device comprising an inflatable balloon.

Figure 22A:
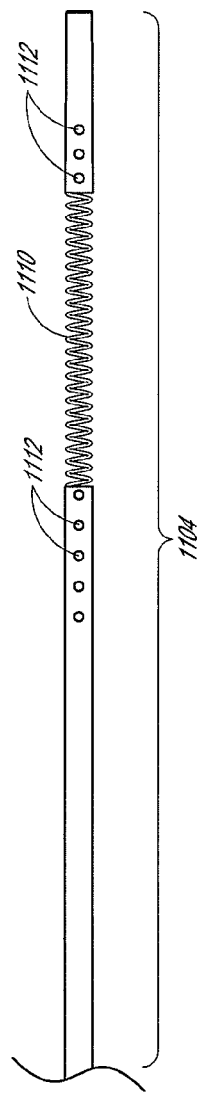
Figure 22B:
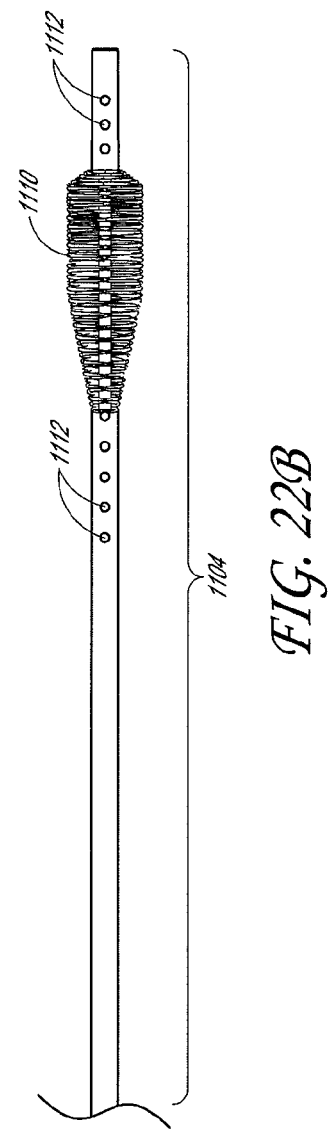

FIGS. 22A and 22B are perspective views of an embodiment of a rapid perfusion device wherein the active segment comprises a radially expandable wire.

FIGS. 23A-23D are perspective views of an embodiment of a rapid perfusion device wherein the active segment comprises a covered or uncovered mesh connected to the microcatheter via tethers.

Figure 23B:
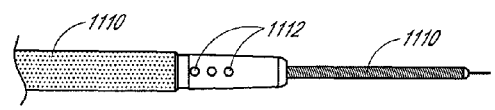
Figure 23A:
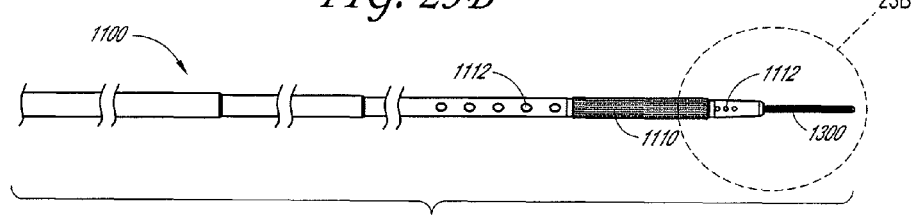
Figure 23D:
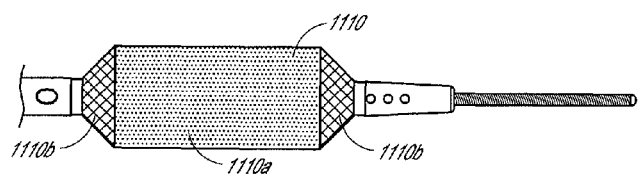
Figure 23C:
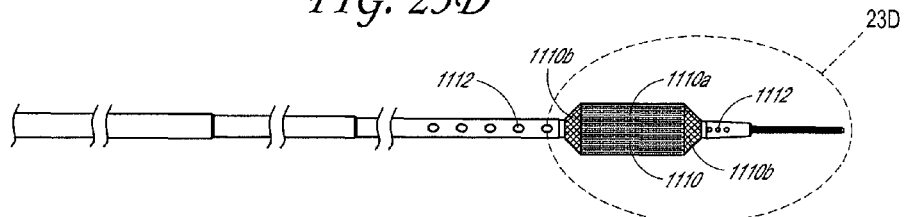
Figure 23E:

FIG. 23E is a side view of an embodiment of an active segment comprising an open braid or covered braid configured to be connected to the microcatheter via tethers or an open braid on both the proximal and distal ends.

FIGS. 24A-24D are perspective views of an embodiment of a rapid perfusion device wherein the active segment comprises a radially expanding wire mesh.

Figure 25:
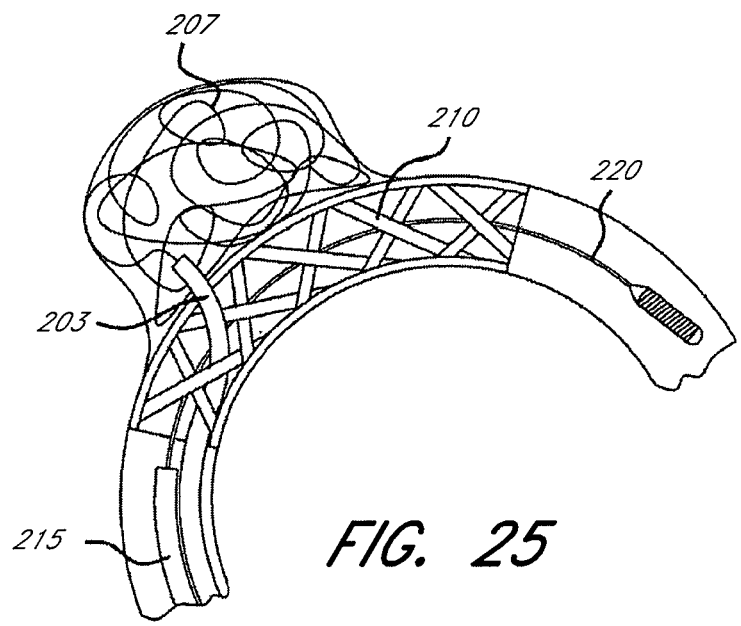

FIG. 25 shows an emplaced temporary tethered stent mechanism bridging the neck of an aneurysm, according to the present disclosure.

Figure 26A:
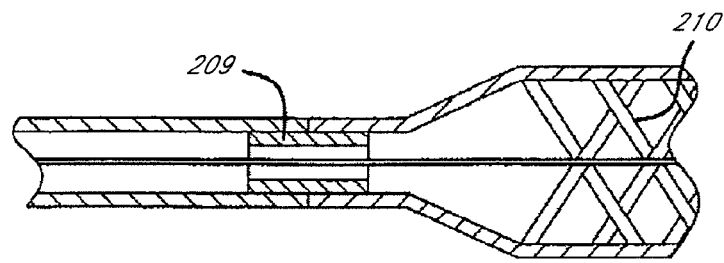

FIG. 26A further illustrates a delivery system according to the instant teachings.

Figure 26B:
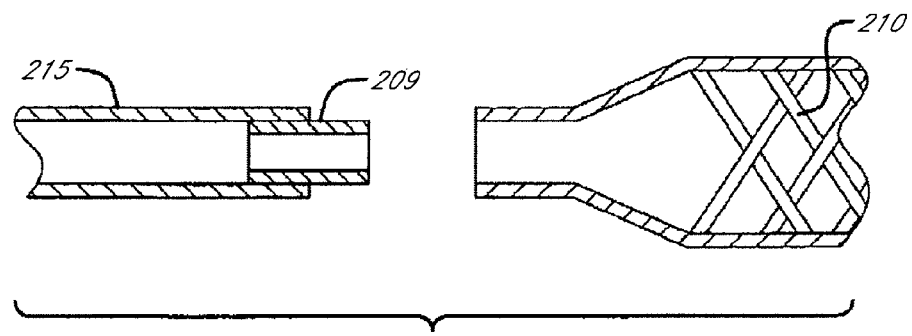

FIG. 26B schematically illustrates additional features according to embodiments of the delivery system of FIG. 26A.

Figure 27A:
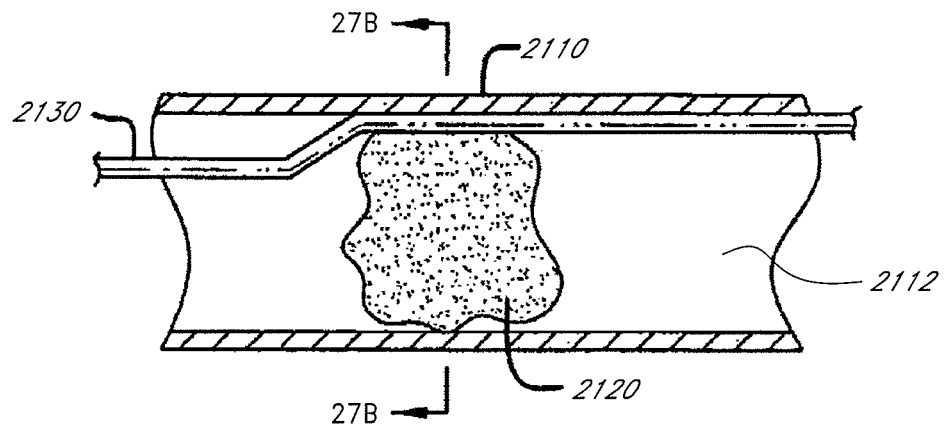

FIG. 27A shows a side view schematic of a microcatheter with wire passing an embolus.

Figure 27B:
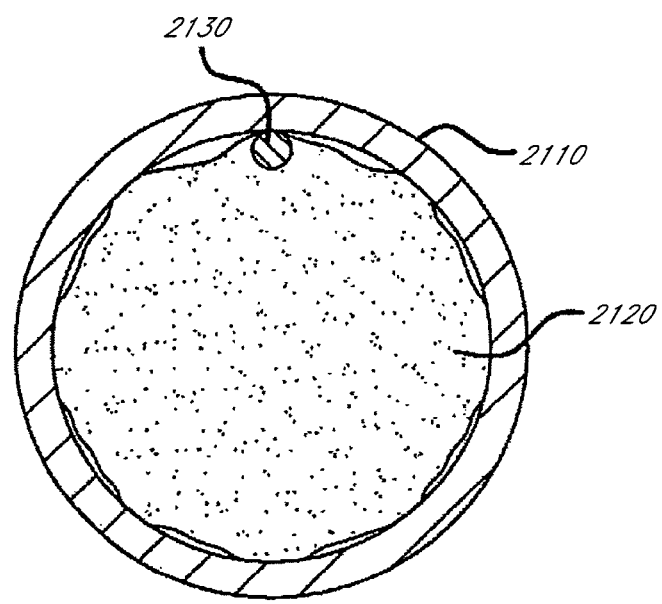

FIG. 27B shows a cross-sectional schematic of an embodiment of a microcatheter wire passing by an embolus at a point of least resistance.

Figure 28:
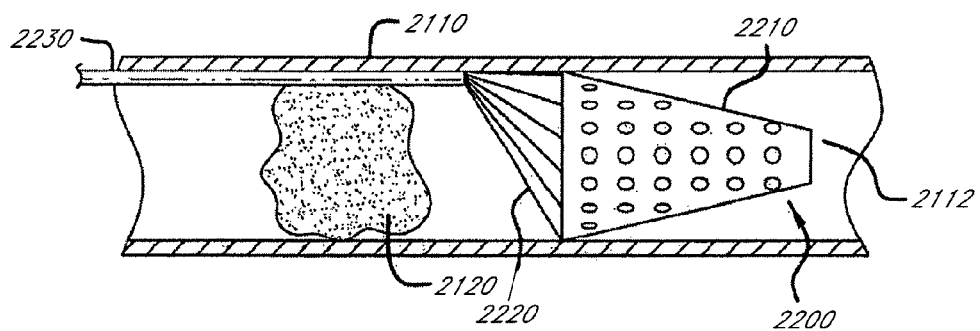

FIG. 28 is a side view of an embodiment of a device for capturing emboli according to the present disclosure comprising a basket for capturing the embolus.

Figure 29:
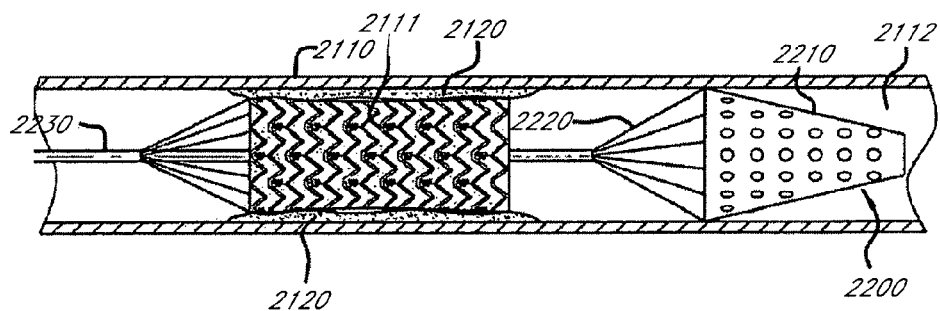

FIG. 29 is a side view of an embodiment of a device for capturing emboli according to the present disclosure used as a safety device in a reperfusion operation.

Figure 30:
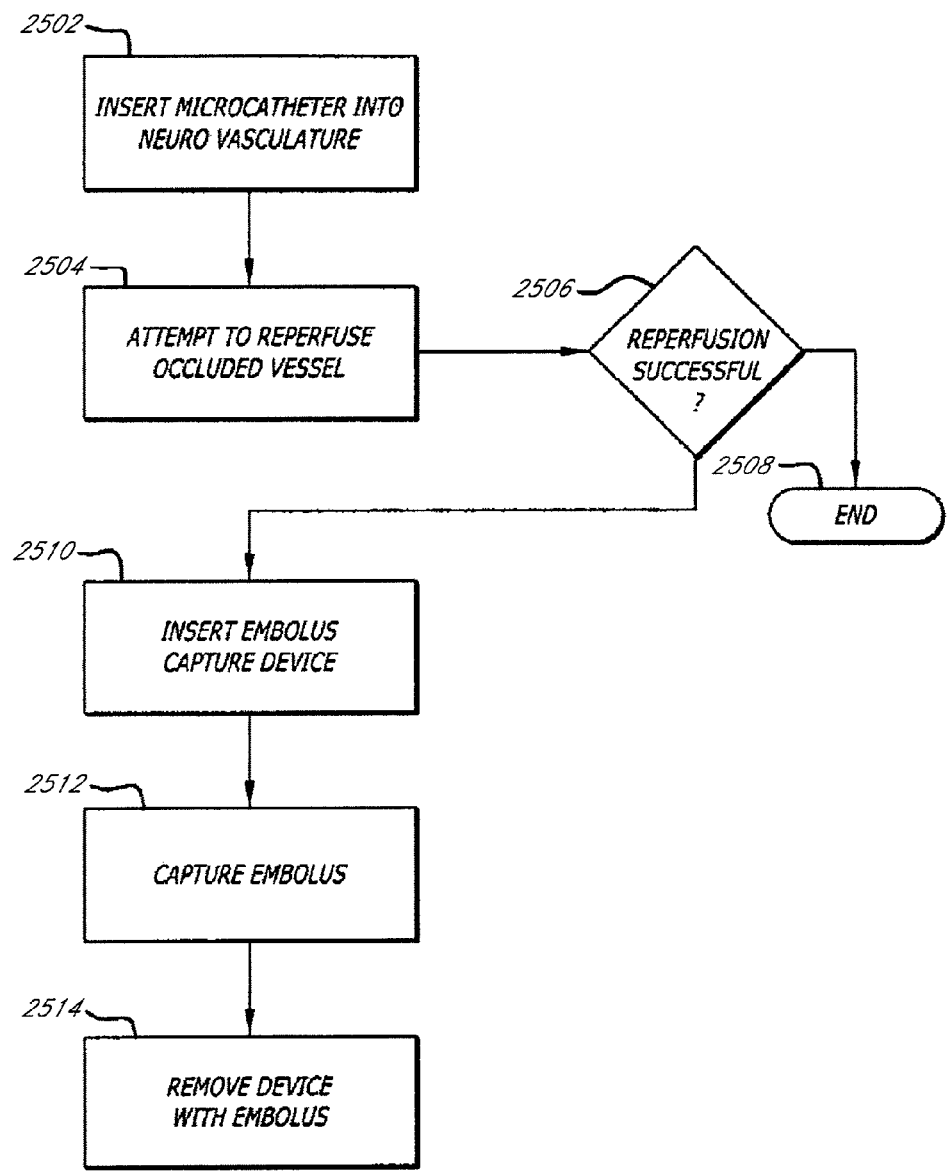

FIG. 30 is a flow diagram of an embodiment of a method wherein an embolus is removed from a patient after a reperfusion operation is unsuccessful.

Figure 31:
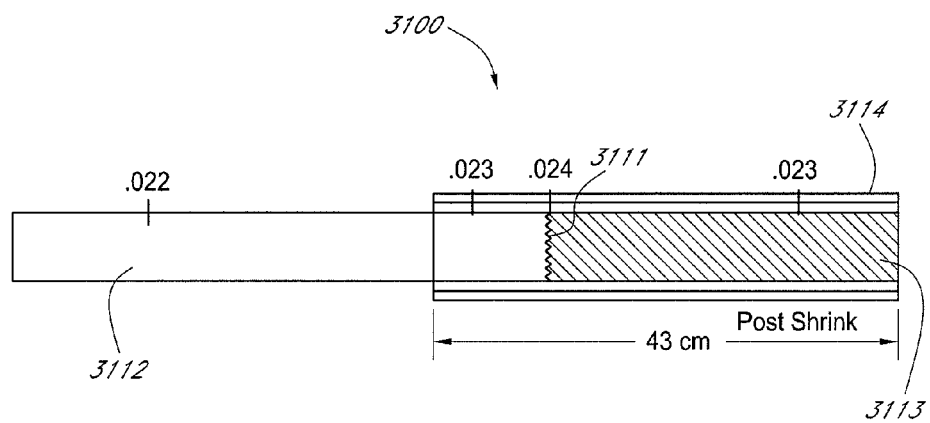
Figure 32:
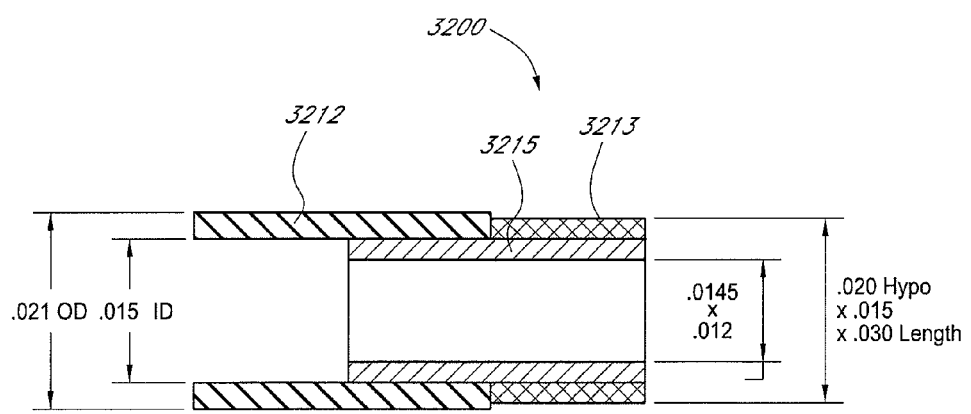

FIGS. 31 and 32 illustrate embodiments of delivery device assemblies.

DETAILED DESCRIPTION OF THE INVENTION

The present inventors have realized that by leveraging a conventional self-expanding revascularization device delivery platform, a poly-modic system can be iterated which impacts, addresses and/or crosses an embolus, radially filters, and either removes the offending embolus or is optionally emplaced to address the same. A paucity of extant systems effective for such combination therapies is noted among the art.

Using endovascular techniques self-expandable tethered or reconstrainable self-expanding neurological medical devices offer instant revascularization/recanalization of MCAs and related vessels, without any of the traditional concerns associated with stenting, according to embodiments of the present invention.

Expressly incorporated herein by reference are the following U.S. Letters patents and publications, each as if fully set forth herein: 2005/0119684; 2007/0198028; 2007/0208367; U.S. Pat. No. 5,449,372; U.S. Pat. No. 5,485,450; U.S. Pat. No. 5,792,157; U.S. Pat. No. 5,928,260; U.S. Pat. No. 5,972,019; U.S. Pat. No. 6,485,500; U.S. Pat. No. 7,147,655; U.S. Pat. No. 7,160,317; U.S. Pat. No. 7,172,575; U.S. Pat. No. 7,175,607; and U.S. Pat. No. 7,201,770.

The instant system allows for natural lysis, revascularization of the challenged vessels, and importantly radially filters any particulates generated, to obviate the need to be concerned with distal migration of the same, unlike prior systems or applications which include largely "off-label" usages of devices approved only for aneurysms in the brain.

The present disclosure relates to revascularization devices (e.g., reperfusion devices) used to treat, among other things, ischemic stroke. Naturally, therefore, the revascularization devices of the present disclosure are designed to be used in neuro-type applications, wherein the specifications of the present catheters and revascularization devices may be deployed in the blood vessels of the cerebral vascular system. Similarly contemplated for the revascularization systems and catheters of the present disclosure is deployment in other parts of the body wherein the specifications of the present disclosure may be used in other vessels of the body in a non-invasive manner.

According to embodiments, disclosed herein is a catheter-based revascularization system. The revascularization devices of the present disclosure are for revascularization of blood vessels. When the catheter-based revascularization system of the present disclosure is deployed into a blood vessel having an embolus, the revascularization device is expanded thereby opening the vessel so that the vessel can resume proper blood flow.

According to the instant teachings, deployment of the system of the present disclosure, establishes immediate 50% of the diameter of the lumen patency of the vessel being addressed. Among the prior art, no system having adequately small profile with flexibility to promote improved access for in-site treatment is known which may be used as a temporary (not implanted) solution. Those skilled in the art readily understand that detachment methods comprising mechanical, electrical, hydraulic, chemical, or thermal, and others are within the scope of the instant teachings.

Moreover, as the embolus dissolves, either via blood flow or by infusing lytic agents than the guidewire lumen, the deployed revascularization device radially filters larger embolus particles from traveling downstream, thereby reducing the chances of further complications. Once the blood vessel is revascularized, the revascularization device is modified to be in a removable state together with filtered detritus, and the catheter-revascularization system is removed from the blood vessels of the patient.

Likewise, in the event that no resolution of the embolus is noted in the instant revascularization system the inventors contemplate detachment and employment as a stent of the cage-like membrane. Angiographic recanalization has been associated with improvement in clinical outcome in the setting of acute stroke resulting from acute intracranial thrombotic occlusion. Anatomic limitations (tortuous anatomy, length of the occlusion, or location of occlusion) or supply limitations are among the reasons precluding use of prior art systems until the advent of the instant teachings.

Stenting has been used successfully to restore flow after abrupt reocclusion occurring after recanalization with other modalities in previous cases. Stenting has also been reported in cases in which other modalities have failed to recanalize vessels. Even if an underlying stenosis is rarely the cause of stroke, stenting may play a role by morselizing the embolic clot or trapping it against the arterial wall. In several embodiments, the present invention comprises an acute stroke revascularization process that comprises providing a reconstrainable self-expanding microstent system, deploying a self-expanding microstent within a neurological vessel; achieving at least one of revascularization and recanalization of a subject vessel; and removing the self-expanding microstent. In some embodiments, at least one supplemental therapy is also provided, and comprises one or more of the following: pharmacological thrombolytic agents, intraarterial thrombolytics, and mechanical manipulation.

The use of intracranial stents as a method for arterial recanalization during cerebral ischemia caused by focal occlusion of an intracranial vessel has been demonstrated to have benefits in some cases. Despite the use of available pharmacological and mechanical therapies, angiographic recanalization of occluded vessels has not been adequately achieved before stent placement, in most cases.

When SAH and intracranial hematoma occurred in patients in whom balloon-mounted stents were used, they most likely resulted from distal wire perforation. The distal wire purchase needed to navigate a coronary stent into the intracranial circulation may explain the occurrence of these adverse events. Alternatively, multiple manipulations of the Merci® brand of retriever device or expansion of balloon-mounted stents may have induced microdissections in the vessel. Stents designed for intracranial navigation have better navigability and pliability. The Wingspan® brand of stent (Boston Scientific) was designed to have more radial force than the Neuroform® brand of stent and may further improve this technique. However, the act clearly needs to advance further in this area.

IA therapy for stroke has evolved during the past decade. Approval of the Merci® brand of retriever device represents a significant step toward achieving better outcomes in acute stroke for patients not suitable for IV tPA. However, recanalization is not always achieved using this device. Therefore, additional treatment options are required, as offered for consideration herein.

Spontaneous dissection of the internal carotid artery (ICA) is one of the main causes of ischemic stroke in young and middle-aged patients, representing 10% to 25% of such cases. Because infarct due to dissection is mainly thromboembolic, anticoagulation has been recommended to prevent new stroke in patients with acute dissection, provided they have no contraindications. In the acute phase, intravenous recombinant tissue-type plasminogen activator (IV rtPA) given within 3 hours after onset of stroke due to dissection is reportedly safe and effective. However, this often needs supplemental therapy to be effective.

Endovascular treatment with stent deployment for ICA dissection with high-grade stenosis or occlusion may be most appropriate when anticoagulation fails to prevent a new ischemic event. In such cases, the MCA may be patent. However, to compare outcomes of patients with acute stroke consecutive to MCA occlusion due to ICA dissection treated either by stent-assisted endovascular thrombolysis/thrombectomy or by IV rtPA thrombolysis. Stent assisted endovascular thrombolysis/thrombectomy compared favorably with IV rtPA thrombolysis, underscoring the need for the instant device.

The main limitation of this procedure is the immediate need for an experienced endovascular therapist. The number of cases of MCA occlusion due to carotid artery dissection was quite small and represented <10% of patients admitted for carotid dissection. However, despite these promising preliminary results, potential drawbacks related to the procedure must be considered. Acute complications such as transient ischemic attack, ischemic stroke, femoral or carotid dissection, and death have been reported. Other potential hazards of endovascular treatment of carotid dissection could have been observed. On balance, the risk-benefit favors solutions like the present invention.

Most patients with acute cerebrovascular syndrome with MC occlusion consecutive to ICA dissection have poor outcomes when treated with conventional IV rtPA thrombolysis, whereas most patients treated with stent-assisted endovascular thrombolysis/thrombectomy show dramatic improvements. Further large randomized studies are required to confirm these data, which trends likewise are technical bases for the instant systems.

According to embodiments and as illustrated in FIG. 1, catheter-based revascularization system 100 provides a platform for lysing emboli in occluded blood vessels. Accordingly, catheter-based revascularization system 100 generally comprises control end 102 and deployment end 104. According to embodiments, control end 102 is a portion of the device that allows a user, such as a surgeon, to control deployment of the device through the blood vessels of a patient. Included as part of control end 102 is delivery handle 106 and winged apparatus 108, in some embodiments. Those skilled in the art readily understand module 113 (see FIG. 2) is detachable.

According to some examples of the instant system during shipping of catheter-revascularization system 100, shipping lock (not shown) is installed between delivery handle 106 and winged apparatus 108 to prevent deployment and premature extension of revascularization device 124 (see FIG. 2) while not in use. Furthermore, by preventing delivery handle 106 from being advanced towards winged apparatus 108, coatings applied to revascularization device 124 are stored in a configuration whereby they will not rub off or be otherwise damaged while catheter-based revascularization system 100 is not in use.

According to embodiments, agent delivery device 130 provides a conduit in fluid communication with the lumen of the catheter-based revascularization system 100 enabling users of the system to deliver agents through catheter-revascularization system 100 directly to the location of the embolus. The instant revascularization system delivery device may be made from materials known to artisans, including stainless steel hypotube, stainless steel coil, polymer jackets, and/or radiopaque jackets. In one embodiment, the revascularization systems comprise a plurality of apertures 118 allowing infusable lytic agents to exit radially and distally into at least a subject embolus when transmitted through agent delivery device which is in fluid communication therewith. The revascularization systems according to several embodiments herein can comprise radiopacity for imaging purposes.

Accordingly, luer connector 132 or a functional equivalent provides sterile access to the lumen of catheter-based revascularization system 100 to effect delivery of a chosen agent. Artisans will understand that revascularization devices of the present invention include embodiments made essentially of nitinol or spring tempered stainless steel. Revascularization devices likewise may be coated or covered with therapeutic substances in pharmacologically effective amounts or lubricious materials. According to embodiments, coatings include namodopene, vasodialators, sirolamus, and paclitaxel. Additionally, at least heparin and other coating materials of pharmaceutical nature may be used.

Deployment end 104 of catheter-based revascularization system 100 comprises proximal segment 110 and distal segment 120. Proximal segment 110, according to embodiments, houses distal segment 120 and comprises outer catheter 112 that is of a suitable length and diameter for deployment into the blood vessel of the neck, head, and cerebral vasculature. For example in some embodiments, proximal segment 110 is from at least about 100 cm to approximately 115 cm long with an outer diameter of at least about 2.5 French to about 4 French.

Referring also to FIG. 2, distal segment 120 comprises inner catheter 122 and revascularization device 124 (as shown here in one embodiment having uniform cells, variable cells likewise being within other embodiments of the present invention), which is connected to inner catheter 122. Inner catheter 122, according to embodiments, is made from stainless steel coil, stainless steel wire, or ribbon or laser cut hypotube and is of a suitable length and diameter to move through outer catheter 112 during deployment. For example, inner catheter 122 extends from outer catheter 112 38 cm, thereby giving it a total length of between at least about 143 and 175 cm (or between about 143 and 150 cm). The diameter of inner catheter 122 according to the exemplary embodiment is 2.7 French, with an inner diameter of at least about 0.012 to 0.029 inches (or at least about 0.012 to 0.021 inches). The inner diameter of inner catheter 122 may be any suitable diameter provided inner catheter 122 maintains the strength and flexibility to both deploy and retract revascularization device 124. In one embodiment, an inner catheter 122' comprises a variable-pitch hypotube, as shown in FIGS. 3A-D. In some embodiments, the hypotube has an outer diameter of 0.025", 0.022", or 0.016" and an inner diameter of 0.017" or 0.008". In some embodiments, the hypotube comprises a 25TW hypotube or a 31TW hypotube. In one embodiment, the inner catheter 122' comprises a laser-cut, variable-pitch hypotube. Region L comprises a laser cut transition region of the variable-pitch hypotube. Regions P1, P2 and P3 comprise three regions of the variable-pitch hypotube having variable pitch. In one embodiment, the pitch decreases from region P1 to region P2 and from region P2 to region P3.

Referring to both figures, revascularization device 124 is a self-expanding, reconstrictable retractable device tethered to inner catheter 122. Revascularization device 124 may be made from nitinol, spring tempered stainless steel, or equivalents as known and understood by artisans, according to embodiments. Revascularization device 124, according to embodiments and depending on the particular problem being addressed, may be from at least about 3.5 mm to about 50 mm in its expanded state. In an expanded state, revascularization device 124 is designed to expand in diameter to the luminal wall of blood vessel where it is deployed.

As known to artisans, revascularization device 124 may be coated or covered with substances imparting lubricous characteristics or therapeutic substances, as desired. Naturally, the expandable mesh design of revascularization device 124 must be a pattern whereby when revascularization device 124 is retracted, it is able to fully retract into inner catheter 122. The nature of the cell type likewise changes with respect to the embodiment used, and is often determined based upon nature of the clot.

Figure 5:
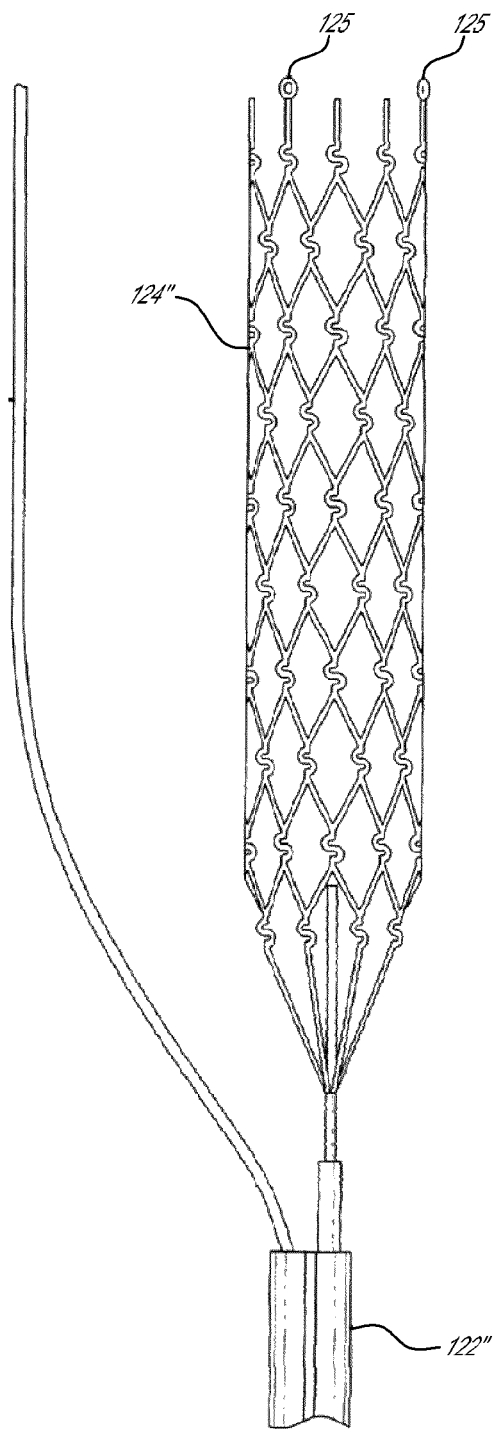
FIG. 5 illustrates an embodiment of a stroke device.

In one embodiment, a revascularization device 124' comprises a plurality of struts 127 and a plurality of open cells 129, as shown in FIGS. 4A-4C. In accordance with some embodiments, recapturability, flexibility and tracking are enabled by the struts of the revascularization device 124', which permit flexion and extension to navigate through curved vessels. FIG. 5 illustrates a stroke device having a revascularization device 124" coupled to a distal end of an inner catheter 122". In one embodiment, a revascularization device 124" comprises one or more markers 125. The markers 125 can comprise at least one marker material selected from the group consisting essentially of platinum and gold. With reference to FIG. 4B, one or more markers can be pressed into pre-laser cut apertures 126 designed to matingly embrace the same.

Catheter-revascularization system 100 is deployed through a patient's blood vessels. Once the user of catheter-revascularization system 100 determines that the embolus to be addressed is crossed, as known and understood well by artisans, revascularization device 124 is deployed by first positioning outer catheter 112 in a location immediately distal to the embolus.

Then, to revascularize/reperfuse the occluded blood vessel, distal catheter 120 is deployed in a location whereby revascularization device 124 expands at the location of the embolus, as illustrated by FIG. 2. The embolus is thereby compressed against the luminal wall of the blood vessel and blood flow is restored. Modular detachable segment 113 is known also, and may be swapped out, as needed, if an Rx system is used.

As discussed above and claimed below, creating a channel for flow ideally includes making a vessel at least about halfway-patent, or 50% of diameter of a vessel being open. According to other embodiments, the channel created may be a cerebral equivalent of thrombolysis in myocardial infarction TIMI 1, TIMI 2, or TIMI 3.

Restoration of blood flow may act as a natural lytic agent and many emboli may begin to dissolve. Revascularization device 124 is designed, according to embodiments, to radially filter larger pieces of the dissolving embolus and prevent them from traveling distal to the device and potentially causing occlusion in another location. Because the revascularization device provides continuous radial pressure at the location of the obstruction, as the embolus dissolves, the blood flow continues to increase.

After the embolus is lysed, revascularization device 124 is sheathed into outer catheter 112 and removed from the body. According to embodiments, larger pieces of the thrombus may be retracted with revascularization device 124 after being captured in the radial filtering process. According to embodiments, revascularization device 124 may be detachable whereby the revascularization device 124 may detach from catheter-based revascularization system 100 if it is determined that revascularization device 124 should remain in the patient. As discussed above, illustrated in the Figures, and claimed below according to embodiments, catheter-based revascularization system 100 reconstrainable attachment or attachment by tether may be optionally detachable. Revascularization device detachment methods comprise mechanical, electrical hydraulic, chemical, thermal, and those other uses known to artisans.

Figure 6:
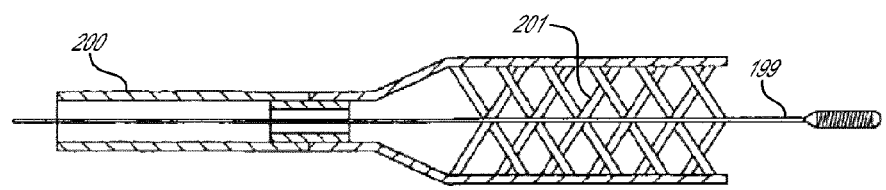
FIG. 6 shows a schematic of a delivery system and exemplary iteration of a temporary tethered stent mechanism according to the present disclosure.

According now to FIG. 6, delivery tube 200 deploys tethered cage-like device/temporary stent 201 prior to embolization, using standard over-the-wire (OTW) system 199.

According to the disclosure, a temporary tethered cage-like structure/tethered stent 201 is non-detachable in some embodiments but attached either to a hypotube or guide wire 199 allowing it to be navigated into tortuous vasculature in the brain. Device 201 may be attached to guide wire 199 or tube 200.

FIG. 7 likewise provides further details of the instant system, with tethered cage-like structure/temporary stent 201 being released from delivery tube 200 using known OTW techniques.

The delivery tube 200 is a variable stiffness tube that is able to track to and through the tortuous anatomy of the cerebral vasculature (i.e., internal carotid artery, MCA, ACA, vertebral and basilar).

The delivery tube 200 can be one or two pieces but must have greater proximal pushability (stiffness) & greater distal flexibility (softness) to allow tracking to distal cerebral arteries.

The delivery tube 200 should also have a lumen that enables tracking over a guide-wire. This feature provides a few benefits; ability to track and be delivered; ability to maintain access in the event different size devices need to be exchanged; provide support to arterial tree during device deployment and recovery. A flexible device may tend to herniate or prolapse into openings. The guide wire provides a pathway (concentric) to the artery and supports the device preventing such technical complications.

The delivery tube 200 can be mechanically attached to the tethered stent by soldering, welding or press fitting. Likewise, those skilled in the art readily understand their attachment mechanisms.

The cage-like structure/stent is made of nitinol to allow it to be compressed and loaded into an introducer for packaging. Similarly memory-based materials likewise function, in accordance with the instant systems.

By attaching it to a delivery wire, the cage-like structure/stent can be placed, retracted, repositioned and recaptured into a microcatheter.

FIGS. 8A-8D illustrate an embodiment of a revascularization device 800 configured for eccentric coupling to a pusher. The revascularization device 800 can be tethered to a pusher (e.g., wire or tube) by a plurality of tether lines 802 (also shown, for example, in FIGS. 2 and 2A). In some embodiments, the revascularization device 800 is eccentrically coupled to the pusher (e.g., tethered off-center). In various embodiments, the revascularization device comprises an open proximal end and/or an open distal end and a generally cylindrical body (see, for example, FIGS. 2 and 2A, 4A-4C, and 5-7).

As excerpted from U.S. Provisional No. 60/980,736, filed Oct. 17, 2007, which is hereby incorporated herein by reference, FIGS. 9A-9F, 10A-10C, 11A-11D, 12A-12D, 13A-13C, 14A-14C, 15, 16, and 17A-17F illustrate various embodiments of revascularization devices as described above.

As excerpted from U.S. Provisional No. 60/987,384, filed Nov. 12, 2007, which is hereby incorporated herein by reference, FIGS. 18A, 18B, 19A, 19B, 20A, 20B, 21A, 21B, 22A, 22B, 23A-23E, 24A-24D illustrate various embodiments of rapid reperfusion devices. In one embodiment, a microcatheter having an active segment reperfuses occluded blood vessels above the junction of the subclavian artery and common carotid artery. The microcatheter is used to penetrate emboli. Once an embolus is penetrated, the active segment of the microcatheter is activated, causing it to expand radially and thereby open a channel for restored blood flow in the embolus. The blood's natural lytic action further degrades the embolus in some cases. Therapeutic agents may be administered through the microcatheter to aid in the reperfusion process. Active and passive perfusion are thus both enabled. In one embodiment, a device is disclosed comprising a distal segment having attached thereto a radially expandable active segment, a proximal segment comprising an active segment activator for radially expanding or retracting the active segment, an activation member connecting the active segment activator to the active segment. The distal segment is of a suitable diameter for use above the juncture of the subclavian artery and common carotid artery.

In one embodiment, a method is disclosed comprising providing a microcatheter having at least a distal segment, proximal segment, and active segment for use above the subclavian artery and common carotid artery, wherein the active segment is radially expandable.

In one embodiment, a catheter system for use above the juncture of the subclavian artery and common carotid artery is provided, although other uses are equally appropriate as determined by qualified medical personnel and may be introduced via a guidewire. The device operates as a standard microcatheter during introduction into a patient. The distal segment, which is remotely deployable, has attached to it an active segment that expands radially to reperfuse emboli. After reperfusion, the active segment is returned to its configuration prior to expansion and the entire microcatheter system is removed.

According to embodiments and as illustrated by an exemplary embodiment in FIG. 18A, there is shown microcatheter 1100. Microcatheter 1100 comprises proximal segment 1102 and distal segment 1104. Proximal segment 1102 remains outside of the patient and is used to insert and retract microcatheter 1100, as well as deploy active segment 1110 of distal segment 1104 during operation.

According to embodiments, catheter length and diameter are suitable for inserting into a human patient and capable of reaching a target embolus in the region above the subclavian and common carotid arteries. For example, according to embodiments, microcatheter 1100 is about 150 cm long; proximal segment 1102 is about 115 cm with an outer diameter of about 4 French and distal segment 1104 is about 35 cm with an outer diameter of about 2.7 French. In one embodiment, the microcatheter 1100 is 135 cm long, proximal segment 1102 is 90 cm long, and distal segment 1104 is 45 cm long. In one embodiment, the microcatheter 1100 has an inner diameter of 0.012". The inventors contemplate, according to embodiments a gradual decrease or stepwise in the outer diameter dimension as a function of the distal distance from proximal segment 1102, according to embodiments. For example, proximal segment 1102 is 4 French at the most proximal end and distal segment 1104 is 2.7 French at the most distal end. Disposed between is a segment having one or more intermediate outer diameters between 4 French and 2.7 French, such as 3.4 French and 3.0 French (see FIG. 23A). The inner diameter of microcatheter 1100 is 0.012 to 0.021 inches, according to embodiments, which allows microcatheter to be inserted along a preinserted guidewire or used to infuse therapeutic agents. According to embodiments, the performance of microcatheter is comparable to standard microcatheters and is designed to track over a guidewire through the neuro-vasculature.

According to embodiments, microcatheter 1100 is designed to follow a path of least resistance through a thrombus. Guidewire inserted through a thrombus tends to follow the path of least resistance through the softest parts of each thrombus. When microcatheter 1100 is inserted, it likewise follows this path of least resistance. As blood flow is restored, the natural lytic action further helps to break up the thrombus.

According to embodiments, active segment 1110 comprises a radially expandable woven mesh or coil. The mesh may be made from materials well known and understood by artisans, including polymers, fluoropolymers, nitinol, stainless steel, vectran, or kevlar. Other biocompatible materials that may be woven or coiled are similarly contemplated. Active segment 1110 is, according to embodiments, 5 mm to 50 mm in length when expanded and is designed to substantially return to its preexpansion configuration for removal of microcatheter after reperfusion. In one embodiment, active segment 1110 is 15 mm long.

As indicated above, active segment 1110 comprises a mesh. The mesh comprises a plurality of individual units, having a uniform size or spacing geometry or a variable size or spacing geometry. According to embodiments where the size or spacing geometry is variable, smaller size or spacing geometry is used to provide a tight mesh for expanding a channel through the thrombus. Larger size or spacing geometry units allow from blood flow through active segment 1110. In one embodiment, active segment 1110 comprises a woven polymer mesh that is heparin coated. In one embodiment, active segment 1110 has a suitable porosity to permit blood flow when expanded. In one embodiment, releasing expansion of active segment 1110 will trap thrombus in the mesh.

According to embodiments, variable cell size or spacing geometry is accomplished with points where the braid crosses over fixed filaments (PICS). Thus, the cell size or spacing geometry varies by varying the density of the braid. Where high radial force is needed to open a channel in an embolus, for example, the filaments of the mesh are denser and therefore cross each other more often, yielding small cell size or spacing geometry that leads to the application of greater radial force when the mesh expands. Where perfusion is desired, the PICS are less dense and the resulting cell size or spacing geometry is increased. Additionally, drug delivery through microcatheter will be more effective in mesh configurations having a large size or spacing geometry.

Active segment 1110 may be coated or covered with substances, such as lubricious agents or pharmacologically active agents, according to embodiments. For example, active segment 110 may be covered with heparin or other agents that are used in clot therapy, such as those that aid in dissolving clots or mitigating vasospasms.

According to similar embodiments, therapeutic agents are deployable through the lumen of microcatheter 1100, thereby allowing users of microcatheter 1100 to determine on a case-by-case basis whether to administer an agent. Accordingly, the braid/geometry of active segment 1110 is porous to allow the agent to pass from lumen of microcatheter 1100 into the blood vessel at the site of an embolus, for example.

Activation member 1120, according to embodiments, is a wire that connects proximal segment 1102 to distal segment 1104 and allows a user of microcatheter 1100 to deploy active segment 1110. Accordingly, activation member 1120 is made from stainless steel wire or braid, composites polymers and metal braids, ribbon or wire coils. According to embodiments, activation member 1120 comprises a hollow lumen that slidably moves over a guidewire to insert microcatheter 1100.

When active segment 1110 is expanded in a vessel, the radial expansion causes a channel to be formed in a thrombus for restored blood flow past the occlusion and thereby reperfuse the vessel. Activation of active segment 1110 is accomplished by mechanical methods, such as with activation member 1120 or by using liner of microcatheter 1110. Use of the liner is accomplished by leaving the liner unfused with active segment 1110.

For example, activation member 1120 fuses to the distal-most portion of activation segment 1110. According to embodiments, activation segment 1110 is heat set into a native confirmation in an expanded state. When activation member 1120 tensions active segment 1110, its confirmation changes from an expanded state into a deliverable state. Once delivered to the site of an embolus, activation member 1120 is adjusted to allow active segment 1110 to relax and thereby expand. According to similar embodiments, active segment 1110 is heat set into a native unexpanded confirmation. Activation member 1120 is used to tension active segment 1110 when delivered to the site of an embolus, thereby expanding it.

Other activation methods include electrical, chemical, and thermal activators, as is known and understood by artisans. Hydraulic activation may be accomplished with a balloon in the interior of the catheter that is filled with a fluid, thereby expanding the balloon, which expands active segment.

According to embodiments illustrated in FIG. 19A, microcatheter is inserted into a vessel having an occlusion. As previously discussed, microcatheter is insertable along a guidewire through vessel lumen 1202, according to certain embodiments. Microcatheter 1100 penetrates embolus 1210 in vessel 1200. Active segment 1110 is positioned to coincide with the position of embolus 1210, according to techniques well known and understood by artisans. Thereafter, active segment 1110 is expanded, thereby opening a channel in thrombus 1210 and restoring blood flow, as illustrated in FIG. 19B.

Once activated, active segment 1110 allows blood to flow around microcatheter 1100 and active segment 1110 to create therapeutic benefits associated with reperfusion. For example and according to embodiments, the portions of distal segment 1104 immediately proximal and distal to active segment 1110 may have a diameter of 2.0 French to 3.0 French and have installed therein revascularization ports 1112, as shown in FIGS. 19A and 19B. Revascularization ports 1112 comprise openings in microcatheter 1100 that allow to blood flow through microcatheter 1100. Additionally, revascularization ports 1112 provide additional delivery points for therapeutic agents delivered through microcatheter 1100.

According to embodiments, a filter may be placed distal of active segment to prevent embolus pieces detached in the reperfusion process from escaping and causing distal occlusions. Accordingly, active segment is designed to capture pieces of embolus during the reperfusion processes. These pieces are captured within active segment 1110 when active segment 1110 is returned to its initial confirmation after expansion.

In some embodiments, active segment 1110 comprises an infusable microwire with an integrated filter as illustrated in FIG. 20A. In one embodiment, the infusable microwire has a diameter of 0.014". According to embodiments and as illustrated in FIG. 20B, active segment 1110 comprises an infusable coil. In one embodiment, the infusable coil has a diameter of 0.014". Accordingly, active segment 1110 comprises a large portion of distal segment 1104, wherein microcatheter 1100 itself coils when activated to create a channel through an embolus whereby blood flow is restored.

In some embodiments, the rapid reperfusion device comprises an infusable temporary stent as illustrated in FIG. 21A. According to embodiments illustrated by FIG. 21B, an infusable balloon is connected to microcatheter 1100 and comprises active segment 1110. Inflation of the infusable balloon opens a channel through the embolus and begins the lytic process.

FIGS. 22A-24D illustrate exemplary embodiments wherein active segment 1110 comprises different configurations designed to reperfuse an occluded blood vessel. According to embodiments illustrated in FIGS. 22A and 22B, active segment 1110 comprises an expandable coiled wire. The coiled wire may be made from stainless steel wire or braid, composite metal polymers, memory shape alloys such as nitinol, etc., wherein the coil is able to stably expand and return to its original state. As illustrated in FIG. 22A, the diameter of coil is substantially the same as that of microcatheter 1100 when in a nonexpanded state. However, when expanded (as illustrated in FIG. 22B) coil expands radially according to the reperfusion principles disclosed herein. According to embodiments, revascularization ports 1112 provide for increased blood flow through the lumen of microcatheter 1100. Activation of the coil may occur as previously disclosed, for example mechanically using activation member 1120, or by electrical or heat methods, as well known and understood by artisans.

FIGS. 23A-23D illustrate an embodiment of the present disclosure wherein active segment 1110 comprises a tethered mesh. According to this embodiment, active segment 1110 comprises mesh 1110A and tethers 1110B. Mesh is the same as previously described. According to embodiments, mesh comprises an open braid or a covered braid. The covering comprises, according to embodiments, a distal protection mechanism and may be a polymer, such as polyurethane, or other biocompatible cover materials such as ePTFE or related thin film. Tethers 1110B serve to provide structure for mesh 1110A, while providing large openings whereby blood may freely flow from the proximal to distal end of active segment 1110. Those skilled in the art will readily understand that materials for tethers and mesh may be the same, different, or interchangeable, as needed. FIG. 23E illustrates an embodiment of an active segment comprising an open braid or covered braid configured to be connected to the microcatheter via tethers or an open braid at both the proximal and distal end, thereby forming an open proximal end and an open distal end.

As shown in FIGS. 23A and 23B, microcatheter 1100 is inserted along guidewire 1300. In some embodiments, guidewire 1300 is compatible with 0.010" and 0.014". Active segment is initially in a non-expanded configuration. FIGS. 23C and 23D illustrate embodiments of active segment 1110 when extended. In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

Figure 24B:
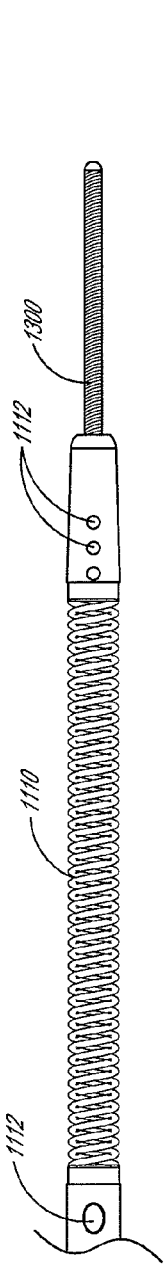
Figure 24A:
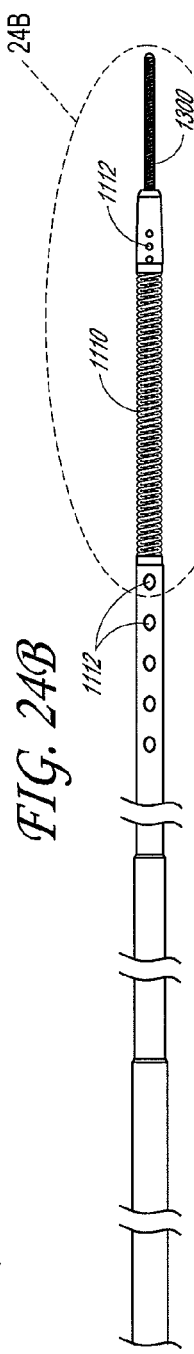
Figure 24C:
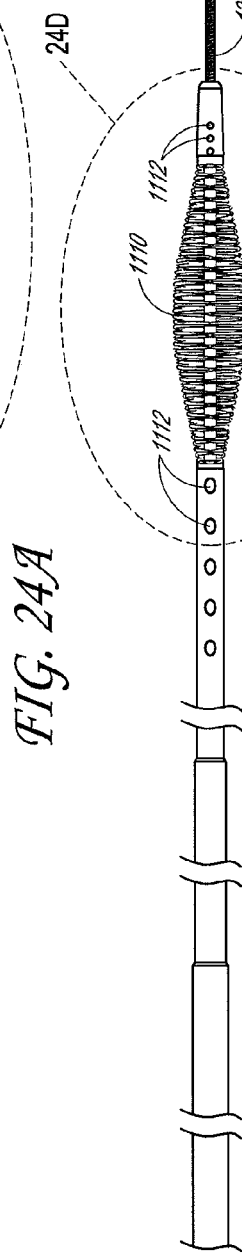
Figure 24D:
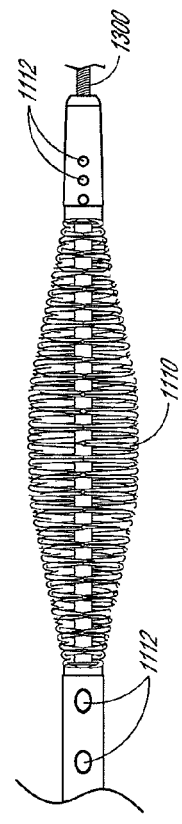

According to embodiments illustrated in FIGS. 24A-24D, active segment 1110 comprises a wire mesh having variable spacing between the wires. FIGS. 24A and 24B illustrate active segment 1110 in a non-expanded configuration. FIGS. 24C and 24D illustrate active segment 1110 in an expanded position, as disclosed herein. In some embodiments, guidewire 1300 is compatible with 0.010" and 0.014". In some embodiments, active segment 1110 has an expanded diameter from 1.5 mm to 3.5 mm and therapeutic lengths of 8 mm, 12 mm, or 16 mm. In one embodiment, microcatheter 1100 has a useable length of 150 cm.

As excerpted from U.S. Provisional Application Ser. No. 60/989,422, filed Nov. 20, 2007, which is hereby incorporated herein by reference, FIGS. 25, 26A and 26B illustrate embodiments of a temporary tethered stent mechanism and delivery system.

In some embodiments, the devices, methods and systems described herein facilitate and enable reconstruction of a vessel wall at the neck of an aneurysm.

According to embodiments, a tethered cage-like structure functions in conjunction with a coiling microcatheter system, among other things, by stabilizing vessel walls and providing tethered cage-like therapeutic support for treating aneurysms.

According to embodiments, methods and systems function with standard microcatheters to temporarily bridge aneurysmal necks.

According to embodiments, a cage-like structure is tethered to the end of a trackable delivery distal system. By bridging the neck of an aneurysm while permitting flow, coil embolization, for example, can be performed without risking vessel embolization. The tethered cage-like structure can then be proximally withdrawn.

The present inventors have discovered novel ways to treat aneurysms. In short, better treatment options can be offered for consideration than traditionally available, as discussed below. According to embodiments illustrated in FIGS. 6, 7, 25, 26A and 26B, the system is optimized in a support role with other therapies.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the microcatheter is placed within the sac of the aneurysm, and the microcatheter is used to place embolic material into the sac of the aneurysm. The embolic material includes, for example, detachable coils or an embolic agent, such as a liquid polymer. The placement of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being placed. Therefore, there is a risk of overfilling the aneurysm in which case the detachable coils also herniate or prolapse into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus the aneurysm can recanalize.

Embolic agent migration is also a problem. For instance, where a liquid polymer is placed into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon.

Thus, there is an increased risk that the detachable balloon will rupture the sac of the aneurysm. Further, detachable balloons can rupture and migrate out of the aneurysm.

Cerebral aneurysms occur in approximately 2% of the population. Approximately 30,000 aneurysms are treated annually in the USA. Aneurysms grow from a weakness in a blood vessel. Origins of aneurysms are presently unknown but linked to hypertension and injury.

About 80% of aneurysms are less than 10 mm with the remainder growing to as large as 40 mm. Most large aneurysms have wide necks characterized with a neck greater than 4 mm or a dome to neck ratio less than 2:1.

In cases when aneurysms have a wide neck, either stent-assisted coiling in practice or balloon remodeling is performed to embolize the aneurysm. During stent-assisted coiling, a stent (for example, the Boston Scientific® brand of Neuroform™ system or the Johnson and Johnson Cordis® Enterprise™ brand of) structure is placed within the artery of the vessel with the aneurysm in an attempt to reconstruct the vessel wall at the neck of the aneurysm.

Patients are typically anti-coagulated and anti-aggregated with a combination of aspirin and Plavix® to mitigate the thrombo-embolic effects of a foreign body response. The patients will maintain the drug regimen long after the embolization procedure.

However, patients with sub-arachnoid hemorrhage (SAH) are not candidates for stents due the prophylactic drug regimen to mitigate the thrombo-embolic complications. A second approach is to perform balloon-remodeling. In this technique, a very soft, conformable balloon (the ev3 brand of Hyperform™ device) typically used for balloon-test-occlusion is placed in the artery at the neck to reconstruct the neck at the aneurysm origin. However, during this technique, flow arrest is performed while the balloon is inflated.

There is a risk of initiating an ischemic event during balloon remodeling and/or a thrombo-embolic event during flow arrest. This technique can be used during SAH because no additional prophylactic drug regimen is required. Once both these techniques are performed, coil embolization of the aneurysm can be performed. During the stenting procedure, the stent is permanently implanted. During balloon remodeling, the balloon is removed once embolization is completed.

A device that can reconstruct the vessel wall at the aneurysm neck origin has been created by tethering a cage-like structure to the distal end of a trackable delivery system. For example, the MindFrame® brand of cage-like structure tethered stent can be placed across the neck of aneurysm without prophylactically administered aspirin and Plavix® as well as not obstructing flow. The tethered stent allows perfusion through the body of the structure and provides support to the neck of the aneurysm allowing coil embolization procedure the tethered stent can be withdrawn proximally into the standard delivery microcatheter.

The device is delivered through standard microcatheters currently available to the interventionalist. An embolization microcatheter can either be placed into the aneurysm prior to placement of the tethered stent or after placement of the tethered stent. If the latter is preferred then the coil embolization microcatheter must be placed through the struts of the tethered stents to access the body of the aneurysm to commence coiling. Both techniques are performed during standard stenting procedures.

Referring back to FIG. 6, delivery tube 200 deploys tethered cage-like device/temporary stent 201 prior to embolization, using standard over-the-wire (OTW) system 199. The instant system is able to be deployed prior to embolization, used to reconstruct the arterial wall at the aneurysm neck, hold in place emboli material and then be able to be removed after embolization or the aneurysm sac is complete.

The system provides a method to assist in aneurysm embolization that does not restrict blood flow and can be used without placing patients on ASA/Plavix® during embolization. During balloon remodeling, flow arrest is performed. During stenting, patients need ASA/Plavix®.

Referring also to FIGS. 6, 25, and 26A, microcatheter/delivery tube 200 emplaces cage-like temporary stent 201 at aneurysm neck, while a coiling microcatheter 203 accesses an aneurysm, and allows coil 207 to be placed therein. Delivery tube 200 and cage-like temporary stent 201 are known in the art and may include Nitinol or the like "super-elastic" materials.

FIG. 26A and FIG. 26B likewise show intermediate steps, whereby placement of the system allows an aneurysm to be isolated, at the neck, whereby coils 207 may be used. According to embodiments illustrated by FIG. 26B, if coil 207 somehow gets caught in stent 201, it may be impossible to remove the device without causing damage to or rupturing the vessels. Therefore, according to embodiments, stent 201 may be detachable, enabling it to be left in the vessel in the event a complication where it cannot be safely removed.

The cage-like structure/stent is made of Nitinol to allow it to be compressed and loaded into an introducer for packaging. Similarly memory-based materials likewise function, in accordance with the instant systems.

The introducer enables the device to be transferred into a microcatheter and deploy to a trusted location such as an aneurysm neck.

The cage-like structure/stent is attached to the delivery wire described previously.

By attaching it to a delivery wire, the cage-like structure/stent can be placed, retracted, repositioned and recaptured into a microcatheter.

This is an important feature. The device, being temporary, allows for the following: 1) perfusion of blood through artery during coiling; 2) perfusion from coiling herniation or prolapse; and 3) removal of the device, mitigating the use of Aspirin and Plavix.

A technical basis for the term "super-elastic" found in the class of nickel-titanium alloys known as "nitinol" alloys discovered by the United States Navy Ordinance Laboratory. These materials are discussed in length in U.S. Pat. Nos.; U.S. Pat. No. 3,174,851 to Beuhler, et al; U.S. Pat. No. 3,351,463 to Rozner, et al; and U.S. Pat. No. 3,753,700 to Harrison, et al. Alloys known to be suitable for this invention are those containing at least 1.5% (wt) and up to about 85% (wt) or more, of one or more alloying members selected from the group consisting of vanadium, chromium, manganese, iron, and cobalt. By the term "stent" or "ribbon", we intend to include elongated shapes, the cross section of which are not square or round and may typically be rectangular, oval, or semi-oval. They should have an aspect ratio of 0.05 (thickness/width) or less, depending on application at issue. Other disclosure can be found in U.S. Provisional No. 60/989,422, which is expressly incorporated herein by reference.

As excerpted from U.S. Provisional Application Ser. No. 61/015,154, filed Dec. 19, 2007, which is hereby incorporated herein by reference, FIGS. 27A, 27B, and 28-30 illustrate embodiments of a device and method for capturing emboli and FIGS. 31 and 32 illustrate delivery device assemblies.

In some embodiments, the devices, methods, and systems described herein facilitate and enable treatment of ischemic or hemorrhagic stroke. More specifically, a tethered basket-like system operates in conjunction with a microcatheter system, to provide arterial support and capture emboli.

In one embodiment, a device for the removal of emboli is disclosed comprising a mesh capturer having at least an undeployed state and a deployed state, the mesh capturer being inserted into the neurovasculature in an undeployed state and removed from the microvasculature in its deployed or retracted state. wherein the mesh capturer is deployed into its deployed state distal to an embolus and advanced proximally until the embolus is substantially contained within the mesh capturer; and wherein the basket is deployed above the subclavian artery and common carotid artery. In some embodiments, the device is inserted into the vasculature over a guidewire. In some embodiments, the device is inserted into the vasculature as a component of a rapid exchange system.

In one embodiment, a method for removing an embolus is disclosed comprising inserting a microcatheter and guidewire distal to an embolus; inserting a embolus capture device over the wire through the microcatheter distal to the embolus; deploying the embolus capture device; retracting the deployed embolus capture device until the embolus is substantially contained within the embolus capture device; and removing the embolus capture device. In some embodiments, the embolus capture device is deployed over a guidewire.

The present inventors have realized that by leveraging a conventional self-expanding reperfusion device delivery platform, a poly-modic system can be iterated which crosses an embolus, filters, and either removes the offending embolus or is optionally emplaced to address the same. A paucity of extant systems effective for such combination therapies is noted among the art.

According to embodiments of the system illustrated in FIGS. 27A, 27B, and 28-30, the system allows for natural lysis, perfusion of the challenged vessels, and importantly filters any particulates generated, to obviate the need to be concerned with distal migration of the particulates generated. In some embodiments, the emboli removal devices are used to treat, among other things, ischemic stroke. Naturally, therefore, the emboli removal devices of the present disclosure are designed to be used in neuro-type applications, wherein the specifications of the present catheters and emboli removal devices may be deployed in the blood vessels of the cerebral vascular system. Similarly contemplated for the emboli removal systems and catheters of the present disclosure is deployment in other parts of the body wherein the specifications of the present disclosure may be used in other vessels of the body in a non-invasive manner. According to embodiments illustrated in FIGS. 27A, 27B, and 28-30, disclosed herein are devices and methods of the removal of neurocranial emboli without causing distal complication arising from the passing of larger pieces of a recovered embolus distal to the location of the original embolus.

According to embodiments illustrated in FIGS. 27A, 27B, and 28-30, disclosed herein is a catheter-emboli removal system. The emboli removal devices of the present disclosure are for reperfusion of blood vessels. When the catheter-emboli removal system illustrated in FIGS. 27A, 27B, and 28-30 is deployed into a blood vessel having an embolus, the emboli removal device is expanded and moved proximally along the vessel so that the embolus is substantially contained with the mesh basket of the emboli removal device.

In one embodiment, deployment of the system illustrated in FIGS. 27A, 27B, and 28-30 establishes immediate 50% of the diameter of the lumen patency of the vessel being addressed by removing the embolus occluding the vessel. Among the prior art, no system having adequately small profile with flexibility to promote improved access for in-site treatment is known which may be used as a temporary (not implanted) solution and removed without substantial damage to the vasculature.

Additionally, in reperfusion applications the emboli removal device may be deployed as a safety device. As the embolus lyses, the deployed emboli removal device filters larger embolus particles from migrating distally, thereby reducing the chances of further complications. If reperfusion is unsuccessful, then the emboli removal device is retracted proximally, thereby substantially capturing the embolus. Then the entire device is removed together with the microcatheter.

According to embodiments and as illustrated in FIG. 27A, a cross sectional view of an artery 2110 having embolus 2120 in artery lumen 2112 is shown. Guidewire 2130 inserted through a thrombus tends to follow the path of least resistance through the softest parts of embolus 2120. When a microcatheter is inserted along guidewire 2130, it likewise follows this path of least resistance. Accordingly, when a stent or embolus capture device is inserted via guidewire 2130, it is deployed offset because guidewire 2130 is not centered in the vessel in many cases, as illustrated in FIG. 27B.

To address the problem of the guidewire offset, the inventors devised an embolus capture device 2200 that is adept at capturing embolus 2120 even when deployed in an offset way. As part of the embolus capture device 2200 design, pieces of embolus 2120 that break away from embolus 2120 are recaptured to prevent potential migration more distal in the vasculature which may potentially cause other emboli, too remote to safely address.

As illustrated in FIG. 28, blood vessel 2110 is shown having vessel lumen 2112 and embolus 2120. As illustrated, embolus capture device 2200 is deployed for capture of embolus 2120. As illustrated, embolus capture device 2200 is deployed along an offset guidewire. However, embolus capture device 2200 is designed for offset deployment to deploy such that it occupies about the center of vessel 2110, which ensure maximum efficiency in the capture of embolus 2120. It will be readily recognized that the devices of the present disclosure need not be deployed offset.

Embolus capture device 2200 comprises mesh basket 2210 and tethers 2220 which are deployed from microcatheter 2230. Mesh basket 2210 comprises a radially expandable woven mesh or coil basket open on the proximal end and closed at the distal end. The mesh may be made from materials well known and understood by artisans, including polymers, fluoropolymers, nitinol, stainless steel, vectran, or kevlar. Other biocompatible materials that may be woven or coiled are similarly contemplated. Mesh basket 2210 connects to microcatheter 2230 via tethers 2220 and is designed to be compatible such that it is removable in its deployed state without causing dissection or other damage to the vasculature.

Mesh basket 2210 comprises a plurality of individual units, having a uniform size or spacing geometry or a variable size or spacing geometry. According to embodiments where the size or spacing geometry is variable, smaller size or spacing geometry is used to provide a tight mesh for preventing the passage of small pieces of embolus 2120 that break away. Larger size or spacing geometry units allow from blood flow 2110. In all cases, size or spacing geometry will not allow pieces of embolus 2120 that may cause potential complications.

Tethers 2220 serve to provide structure for mesh basket 2110, while providing large openings whereby blood may freely flow from the proximal to distal end of embolus removal device 2200. According to embodiments, tethers 2220 are made from the same material as mesh basket 2210. Those skilled in the art will readily understand that materials for tethers and mesh may be the same, different, or interchangeable, as needed.

During deployment of embolus capture device 2200, mesh basket is stored in microcatheter 2230 in an undeployed state. In the undeployed state, microcatheter 2230 is advanced distal to embolus 2120 and mesh basket 2210 is deployed. According to embodiments, both mesh basket 2210 and tethers 2220 are deployed distal to embolus 2120 to prevent tethers 2220 from dislodging pieces of embolus 2120 prior to full expansion of mesh basket 2210, thereby preventing the pieces from advancing distal to the embolus 2120 before mesh basket 2210 is in place to filter them.

After deployment, according to embodiments, embolus removal system 2200 is retracted proximally until embolus is substantially contained within mesh basket 2210. Thereafter, mesh basket 2210 and microcatheter 2230 are removed from the vasculature of the patient. During removal of mesh basket 2210 and microcatheter 2230, embolus 2120 is trapped within mesh basket 2210 and withdrawn from vessel 2110.

According to embodiments, microcatheter 2230 length and diameter are suitable for inserting into a human patient and capable of reaching a target embolus in the region above the subclavian and common carotid arteries. For example, according to embodiments, microcatheter 2230 is about 150 cm long; microcatheter has a proximal segment (at a control end of microcatheter 2230) that is about 115 cm long with an outer diameter of about 3.5 French and a distal segment (at a deployment end of microcatheter 2230) is about 35 cm with an outer diameter of about 2.7 French. The inventors contemplate, according to embodiments a gradual decrease or stepwise in the outer diameter dimension as a function of the distal distance from proximal segment, according to embodiments. For example, proximal segment is 3.5 French at the most proximal end and distal segment is 2.7 French at the most distal end. Disposed between is a segment having one or more intermediate outer diameters between 3.5 French and 2.7 French, such as 3.2 French and 3.0 French. The inner diameter of microcatheter 230 is 0.012 to 0.029 inches, according to embodiments, which allows microcatheter to be inserted along a preinserted guidewire or used to infuse therapeutic agents. According to embodiments, the performance of microcatheter 2230 is comparable to standard microcatheters 2230 and is designed to track over a guidewire through the neurovasculature.

As illustrated by embodiments in FIG. 29, embolus capture device 2200 may be deployed concurrently with a reperfusion device 2210. As embolus 2120 is reperfused with reperfusion device 2210, embolus capture device 2200 provides a safety feature whereby pieces of embolus 2120 that break away are captured in mesh basket 2210 and removed with the reperfusion device generally. Additionally, as vessel 2110 reperfuses due to natural lytic action, mesh basket 2210 provides a minimum particle size permitted to pass distal to embolus capture device 2200. Consequently, embolus capture device 2200 prevents further complications distal to the original site of the occlusion by preventing larger embolus 2120 pieces or particles from passing deeper into the neurovasculature and occluding it in more distal locations.

Alternately and as illustrated according to embodiments in FIG. 30, reperfusion device is used after reperfusion is unsuccessfully attempted or not successful to the desired level. Accordingly, microcatheter is inserted into the neurovasculature in operation 2502 as well known and understood by artisans. Reperfusion is attempted, for example with the reperfusion device 2210 of FIG. 29 in operation 2504 of FIG. 25.

After reperfusion is attempted, the success is determined in operation 2506. For example, a contrast dye is used to determine the level to which the occluded vessel is reperfused, as is well known to artisans.

If reperfusion is not successful to a desired degree, then embolus capture device 2200 is inserted through the microcatheter as described herein and deployed distal to the embolus 2120. For example, creating a channel for flow ideally includes making a vessel at least about halfway-patent, or 50% of diameter of a vessel being open. According to embodiments, the channel created may be a cerebral equivalent of thrombolysis in myocardial infarction (TIMI) 0, TIMI 1, or TIMI 2, TIMI 3, and thrombolysis in cerebral infarction (TICI) and TICI 3. In these cases, blood flow is not accomplished to a desired degree. It is therefore desirable to remove the entire embolus. Thus, after embolus capture device 2200 is deployed distal to the embolus, it is retreated proximal until embolus 2120 is substantially inside of mesh basket 2210 in operation 2512. Thereafter, mesh basket 2210, embolus 2120, and microcatheter 2230 are removed.

The embolus capture devices of the present disclosure may be designed for over the wire deployment or rapid exchange deployment, according to embodiments.

In one embodiment, ischemic stroke reperfusion or clot capture is performed by a reperfusion device or embolus capture device comprising a NiTi cut tube.

One embodiment for ischemic stroke clot retrieval includes an eccentric design. This embodiment addresses the problem during clot removal of the thrombectomy device being forced off-center because of microcatheter positioning after the microcatheter/guidewire passes the embolus. This "off-centering" causes the device to miss the embolus when pulled proximal to attempt to capture it or fragmenting will occur because the device will shave the embolus. In some embodiments, an off center delivery system is used to capture the embolus. In some embodiments, the struts are designed or favored to the periphery of the artery as opposed to the center of the artery. In some embodiments, the struts are designed to accumulate in 270 degrees of the thrombectomy device allowing open space for the embolus to fall into. By making the attachment point off-center, the open area is increased. By making the device off-center from the point of attachment to the delivery system, the device must increase the chance of capturing the embolus, which is also off-center from the microcatheter.

The chart below illustrates several ischemic stroke delivery system assembly embodiment options:

| 1st Option | | 2nd Option | |
|---|---|---|---|
| Hypo: (24 TW) | .022" × .014" | Hypo: | .0215" × .0155" |
| Ribbon Coil: | .003" × .005" × .015" | Ribbon Coil: | .003" × .005" × .015" |
| PET Heat Shrink: | .027" × .00025" Wall | PET Heat Shrink: | .027" × .00025" Wall |
| or | .028" × .0004" Wall | | |
| 3rd Option | | 4th Option | |
| Hypo: | .022" × .014" | Hypo: | .0215" × .0155" |
| Ribbon Coil: | .003" × .010" × .015" | Ribbon Coil: | .003" × .010" × .015" |
| PET Heat Shrink: | .027" × .00025" Wall | PET Heat Shrink: | .027" × .0025" Wall |
| or | .028" × .0004" Wall | | |

In some embodiments, the delivery systems maintain an outer diameter at the solder joint of 0.024" max. In some embodiments, the PET heat shrink is installed over the distal 45 cm of the delivery device. In some embodiments, the distal tip of the delivery system is trimmed after installation of the PET heat shrink. In some embodiments, the distal and proximal ends of the delivery system are deburred. In some embodiments, the delivery systems must accept a 0.010" guidewire.

FIG. 31 illustrates embodiments of a distal end of a hypotube assembly 3100 that includes a solder joint 3111 between a hypotube 3112 and a ribbon coil 3113 and a PET heat shrink 3114. FIG. 31 illustrates example outer diameter and length dimensions of the delivery system assembly.

The chart below illustrates dimensions for embodiments of the hypotube assembly, or delivery system.

| Design | Hypotube OD | Ribbon Coil | PET | PET Prox | PET @ Joint | PET Distal |
|---|---|---|---|---|---|---|
| 1 | .022" × .014" 24 TW | .003" × .005" × .015" | 0.027" × .00025" × 45 cm | .023" | .024" | .023" |
| 2 | .022" × .014" 24 TW | .003" × .010" × .015" | 0.027" × .0025" × 45 cm | .023" | .024" | .023" |
| 3 | .0215" × .0155" | .003" × .005" × .015" | 0.027" × .0004" × 45 cm | .022" | .025" | .0225"/ .023" |
| 4 | .0215" × .0155" | .003" × .010" × .015" | 0.027" × .0004" × 45 cm | .022" | .025" | .0225"/ .023" |
| 5 | .022" × .014" | .002" × .010" × .017" | 0.028" × .0004" × 45 cm | .022" | .0245" | .023"/ .025" |

The embodiments disclosed in the tables above accept a 0.010 G.W. (guidewire) straight. In some embodiments, the distal tip of the hypotube 3112 is ground (e.g., to 0.0175") to accept the inner diameter (e.g., 0.015") of the ribbon coil 3113. The distal tip of the hypotube 3112 is soldered to the proximate tip of the ribbon coil 3113. The PET 3114 is cut to 45 cm, the heat shrink is heated to 400 degrees Fahrenheit, and restrained while heated.

Example 1

In Vitro Tracking Evaluation Test

A study was performed to evaluate in-vitro tracking of embodiments of delivery system. The testing equipment included: a FlowTek A201 with stroke model, a 5F CORDIS® ENVOY™ MPD guide catheter, a 135 cm×0.027" inner diameter CORDIS® MASS TRANSIT™ microcatheter, and a 0.010 diameter×200 cm length TRANSEND® guidewire. The study used the following numbered scoring system: (1) pass with no friction at all; (2) pass with acceptable friction; (3) pass with some friction; (4) pass with difficulty; (5) can't pass.

| Design # | Curve 1 | Curve 2 | Curve 3 | Curve 4 | PCOM | A1/M1 | M2/M3 |
|---|---|---|---|---|---|---|---|
| 1 | 2/3 | 2/3 | 2/3 | 2/3 | 2/3 | 2/3 | 2 |
| 2 | 3 | 3 | 3 | 3 | 3 | 3 | 2 |
| 3 | N/A | N/A | N/A | N/A | N/A | N/A | N/A |
| 4 | 2 | 2 | 2 | 2 | 2 | 2 | 2 |
| 5 | 1 | 1/2 | 1/2 | 1/2 | 1/2 | 1/2 | 1/2 |

The following notes were taken from the study regarding guidewire tracking. Design 1 passed fine until the PCOM segment with a score of 4. Design 2 experienced some friction requiring 300 cm of exchange wire with a score of 3/4. Design 4 scored a 5 at curve 4. Design 5 scored a 4 generally. Designs 3 and 4 had a 0.0155" inner diameter and designs 1 and 2 had a 0.014" inner diameter. Design 5 had a 0.002"×0.010"× 0.018" hypotube ribbon coil.

FIG. 32 illustrates an embodiment of a distal end of a delivery system assembly 3200. In one embodiment, the delivery system assembly 3200 includes a proximal hypotube 3212, a distal braid 3213 and a polyimide liner 3215. In one embodiment, the polyimide liner 3215 may be a braid. In one embodiment, the braid needs 0.00065" wire.

Strut thicknesses for the recanalization or reperfusion devices described herein can include 0.0040", 0.0025", 0.0020", and 0.0009". The strut thicknesses may vary. The devices may be used for reperfusion and may be tethered. The devices may or may not be recapturable and may or may not include markers.

In some embodiments, the devices described herein are be used for clot removal and comprise a clot basket or spiral basket. In one embodiment, the clot removal device comprises a woven retrieval basket. The woven retrieval basket may include features such as an over the wire design, low porosity fine wires in the basket area to support a clot (wire dia: 0.035 mm and 56-97 pics/cm), or thicker wires that open the basket and give it tensile strength (wire dia: 0.076 mm). The woven retrieval basket may also be fully automatable.

In another embodiment, a reperfusion catheter device includes a nitinol braid. In one embodiment, the braid includes 24 strands with a wire size of 0.076 mm, a braid angle of 42 degrees, an expanded diameter of 3.5 mm, and a collapsed diameter of approximately 0.030". Other disclosure can be found in U.S. Provisional No. 61/015,154, which is expressly incorporated herein by reference.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A catheter-based acute stroke recanalization system configured to provide instant flow restoration of an occluded blood vessel of cerebral vasculature of a patient, comprising:
   an outer catheter configured to be delivered over a guidewire to a location of an embolus within an occluded blood vessel of the cerebral vasculature of a patient;
   an inner catheter having a length and diameter suitable to be sheathed within the outer catheter, the inner catheter and the outer catheter being longitudinally moveable with respect to each other, wherein the inner catheter is a stainless steel wire or a laser-cut, variable pitch hypotube; and
   a self-expanding nitinol revascularization device coupled to a distal end of the wire or hypotube by a plurality of tethers, the self-expanding nitinol revascularization device having a compressed configuration when the revascularization device is sheathed within the outer catheter and an expanded configuration upon retraction of the outer catheter, the revascularization device comprising a first plurality of struts that form a plurality of rings, and a second plurality of struts that join the plurality of rings, each strut of the second plurality of struts between two adjacent rings being separated from (a) adjacent struts of the second plurality of struts between the two adjacent rings by four struts of the first plurality of struts in each of the two adjacent rings, and (b) another strut of the second plurality of struts positioned on a longitudinally opposing side of a ring of the plurality of rings by a single strut of the first plurality of struts, and, in the expanded configuration, each ring having a smaller diameter than has any proximally adjacent ring;
   wherein, in use, the outer catheter is inserted through the embolus within the blood vessel of the cerebral vasculature and, upon retraction of the outer catheter, the self-expanding nitinol revascularization device transitions to the expanded configuration at the location of the embolus without mechanical actuation to compress the embolus against the luminal wall of the blood vessel to restore blood flow through the blood vessel;
   wherein the revascularization device is a temporary, non-implantable device that is configured to retract back into the outer catheter for removal; and
   wherein each strut of the second plurality of struts has a first end and a second end, the second end being offset from the first end about a circumference of the self-expanding nitinol revascularization device.

2. The acute stroke recanalization system of claim 1, wherein the inner catheter further comprises a polymeric jacket incorporated within the inner catheter to improve trackability of the guidewire.

3. The acute stroke recanalization system of claim 1, wherein said acute stroke recanalization system further comprises a plurality of apertures allowing infusable lytic agents to exit radially and distally into at least a subject embolus when transmitted through agent delivery device which is in fluid communication therewith.

4. The acute stroke recanalization system of claim 1, further comprising radiopacity for imaging purposes.

5. The acute stroke recanalization system of claim 4, said radiopacity further comprising at least one marker material selected from the group consisting essentially of platinum and gold.

6. The acute stroke recanalization system of claim 5, wherein the markers are pressed into pre-laser cut apertures designed to matingly embrace the markers.

7. The acute stroke recanalization system of claim 1, wherein said self-expanding nitinol revascularization device is configured to create a flow channel within the blood vessel of at least about 50% of the diameter of the blood vessel.

8. The acute stroke recanalization system of claim 1, wherein said self-expanding nitinol revascularization device comprises a coating or covering.

9. The acute stroke recanalization system of claim 1, wherein said inner catheter has an inner diameter of at least about 0.012 to 0.029 inches.

10. The acute stroke recanalization system of claim 1, wherein at least a portion of said inner catheter comprises a flexible material configured to permit flexion and extension to navigate through curved vessels of the cerebral vasculature.

11. The acute stroke recanalization system of claim 1, wherein said hypotube comprises a stainless steel hypotube.

12. The acute stroke recanalization system of claim 1, wherein said compression of the embolus against the luminal wall of the blood vessel further comprises morcellation of the embolus.

13. The acute stroke recanalization system of claim 1, wherein a distal segment of the outer catheter has an outer diameter that is less than an outer diameter of a proximal segment of the outer catheter.

14. The acute stroke recanalization system of claim 13, wherein the distal segment has a diameter of 2.7 French and the proximal segment has a diameter of 4 French.

15. A catheter-based acute stroke recanalization system configured to restore blood flow in an occluded blood vessel of cerebral vasculature of a patient, comprising:
an outer catheter configured to be delivered over a guidewire to a location of an embolus within the cerebral vasculature of a patient, the outer catheter having a distal end configured for insertion through the embolus;
an inner catheter having a length and diameter suitable to be sheathed within the outer catheter, the inner catheter and the outer catheter being longitudinally moveable with respect to each other, wherein the inner catheter is a wire or a variable-pitch hypotube; and
a self-expanding revascularization device coupled to a distal end of the wire or hypotube by a plurality of tether lines, at least a portion of the self-expanding revascularization device having a compressed configuration when the revascularization device is sheathed within the outer catheter and an expanded configuration upon retraction of the outer catheter, said revascularization device comprising a first plurality of struts that form a plurality of rings, and a second plurality of struts that join the plurality of rings, each strut of the second plurality of struts between two adjacent rings being separated from (a) adjacent struts of the second plurality of struts between the two adjacent rings by four struts of the first plurality of struts in each of the two adjacent rings, and (b) another strut of the second plurality of struts positioned on a longitudinally opposing side of a ring of the plurality of rings by a single strut of the first plurality of struts, and, in the expanded configuration, each ring having a smaller diameter than has any proximally adjacent ring;
wherein said revascularization device is configured to compress the embolus against a luminal wall of the blood vessel to restore blood flow through the blood vessel to facilitate natural lysis of the embolus;
wherein the revascularization device is a temporary, non-implantable device that is configured to retract back into the outer catheter for removal;
wherein, upon retraction of the outer catheter, the self-expanding revascularization device is configured to transition to the expanded configuration at the location of the embolus without mechanical actuation to compress the embolus against the blood vessel to restore blood flow through the blood vessel; and
wherein each strut of the second plurality of struts has a first end and a second end, the second end being offset from the first end about a circumference of the self-expanding revascularization device.

16. The acute stroke recanalization system of claim 15, wherein said recanalization system comprises one or more apertures to allow infusable lytic agents to contact and lyses the embolus.

17. The acute stroke recanalization system of claim 15, wherein at least a portion of said inner catheter comprises a flexible material configured to permit flexion and extension to navigate through curved vessels of the cerebral vasculature.

18. The acute stroke recanalization system of claim 15, wherein said compression of the embolus against the luminal wall of the blood vessel further comprises morcellation of the embolus.

19. A catheter-based acute stroke recanalization system configured to provide instant flow restoration of an occluded blood vessel of cerebral vasculature of a patient, comprising:
an outer catheter configured to be delivered over a guidewire to a location of an embolus within an occluded blood vessel of the cerebral vasculature of a patient;
an inner catheter being sheathed within and longitudinally moveable with respect to the outer catheter;
a self-expanding device coupled to a distal end of the inner catheter by a plurality of tether lines to facilitate resheathing of the self-expanding device into the outer catheter, the self-expanding device having a compressed configuration in which the -self-expanding device is sheathed within the outer catheter and an expanded configuration upon retraction of the outer catheter for removal, the self-expanding device comprising a first plurality of struts that form a plurality of rings, and a second plurality of struts that join the plurality of rings, each strut of the second plurality of struts between two adjacent rings being separated from (a) adjacent struts of the second plurality of struts between the two adjacent rings by four struts of the first plurality of struts in each of the two adjacent rings, and (b) another strut of the second plurality of struts positioned on a longitudinally opposing side of a ring of the plurality of rings by a single strut of the first plurality of struts, and, in the expanded configuration, each ring having a smaller diameter than has any proximally adjacent ring; and
wherein each strut of the second plurality of struts has a first end and a second end, the second end being offset from the first end about a circumference of the self-expanding device.

20. The acute stroke recanalization system of claim 19, wherein the self-expanding device comprises a stent.

21. The acute stroke recanalization system of claim 19, wherein a distal segment of the outer catheter has an outer diameter that is less than an outer diameter of a proximal segment of the outer catheter.

22. The acute stroke recanalization system of claim 21, wherein the distal segment has a diameter of 2.7 French and the proximal segment has a diameter of 4 French.

* * * * *